US010842401B2

(12) United States Patent
Trayanova et al.

(10) Patent No.: US 10,842,401 B2
(45) Date of Patent: Nov. 24, 2020

(54) SYSTEMS AND METHODS FOR SIMULATION PREDICTION OF TARGETS FOR CATHETER ABLATION OF LEFT ATRIAL FLUTTER IN PATIENTS WITH ATRIAL STRUCTURAL REMODELING

(71) Applicant: THE JOHNS HOPKINS UNIVERSITY, Baltimore, MD (US)

(72) Inventors: Natalia A. Trayanova, Baltimore, MD (US); Sohail Zahid, Baltimore, MD (US); Patrick Boyle, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 279 days.

(21) Appl. No.: 15/573,292

(22) PCT Filed: May 12, 2016

(86) PCT No.: PCT/US2016/032219
§ 371 (c)(1),
(2) Date: Nov. 10, 2017

(87) PCT Pub. No.: WO2016/183385
PCT Pub. Date: Nov. 17, 2016

(65) Prior Publication Data
US 2018/0103865 A1    Apr. 19, 2018

Related U.S. Application Data

(60) Provisional application No. 62/160,518, filed on May 12, 2015.

(51) Int. Cl.
*A61B 5/046* (2006.01)
*A61B 5/00* (2006.01)
(Continued)

(52) U.S. Cl.
CPC ............ *A61B 5/046* (2013.01); *A61B 5/0044* (2013.01); *A61B 5/0059* (2013.01);
(Continued)

(58) Field of Classification Search
CPC ........ A61B 5/046; A61B 5/044; A61B 5/0059
See application file for complete search history.

(56) References Cited

U.S. PATENT DOCUMENTS

2010/0114094 A1   5/2010   Thapliyal et al.
2013/0103064 A1   4/2013   Arenson et al.
(Continued)

FOREIGN PATENT DOCUMENTS

KR   10-2007-0012074 A   2/2007
KR   10-2007-0027494 A   3/2007

*Primary Examiner* — Joseph M Dietrich
(74) *Attorney, Agent, or Firm* — Johns Hopkins Technology Ventures

(57) ABSTRACT

A computer-implemented method for non-invasively identifying ablation locations in atrial tissue, can include: receiving three-dimensional imaging data representing atrial tissue of a left atrial flutter (LAFL) subject; generating a subject-specific model of the at least one of the atrial tissue from the three-dimensional imaging data; estimating tissue fiber orientations in the atrial tissue; assigning the estimated tissue fiber orientations to the subject-specific model of the atrial tissue; conducting simulations of LAFL using the subject-specific model to identify regions of slow conduction of a propagating wave within an atrial tissue region of the atrial tissue; a critical isthmus of a rotational wavefront within the atrial tissue region; or a region based on a minimum cut in a flow network; and identifying at least one ablation location in the atrial tissue region based on the identified regions of slow conduction, the critical isthmus, or the minimum cut.

14 Claims, 20 Drawing Sheets

UTAH I

(51) Int. Cl.
*A61B 18/14* (2006.01)
*A61B 18/00* (2006.01)

(52) U.S. Cl.
CPC .......... *A61B 5/0073* (2013.01); *A61B 5/0082* (2013.01); *A61B 18/1492* (2013.01); *A61B 5/0035* (2013.01); *A61B 2018/00357* (2013.01); *A61B 2018/00577* (2013.01); *A61B 2018/00839* (2013.01); *A61B 2576/023* (2013.01)

(56) References Cited

U.S. PATENT DOCUMENTS

| | | | |
|---|---|---|---|
| 2014/0058246 A1* | 2/2014 | Boveja | A61B 5/0452 600/411 |
| 2014/0122048 A1* | 5/2014 | Vadakkumpadan | G06T 7/11 703/11 |
| 2014/0200575 A1 | 7/2014 | Spector | |

* cited by examiner

FIG. 6A LGE-CMR
FIG. 6B SEGMENTATION
FIG. 6C 3D MODEL
FIG. 6D FIBER ORIENTATION
FIG. 6E MODELING ATRIAL ELECTROPHYSIOLOGY

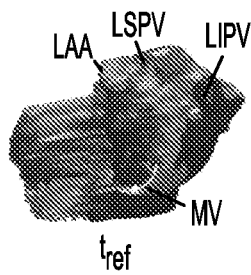
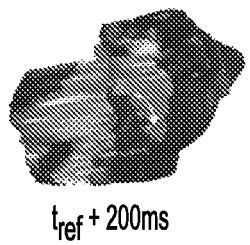
FIG. 13A    FIG. 13B
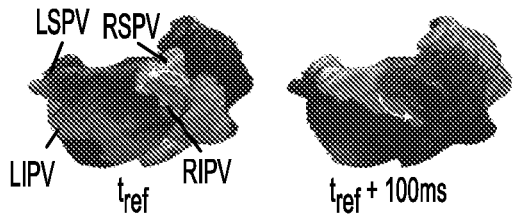
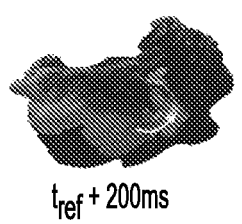
FIG. 13C    FIG. 13D
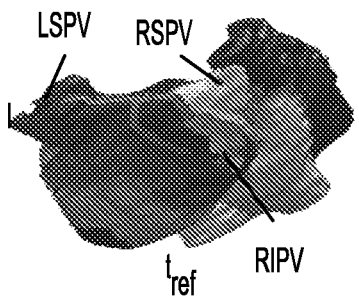
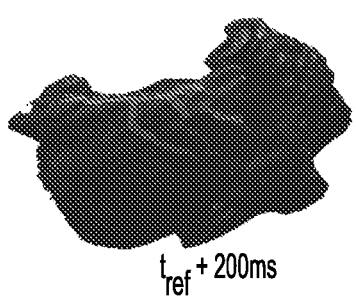
FIG. 13E

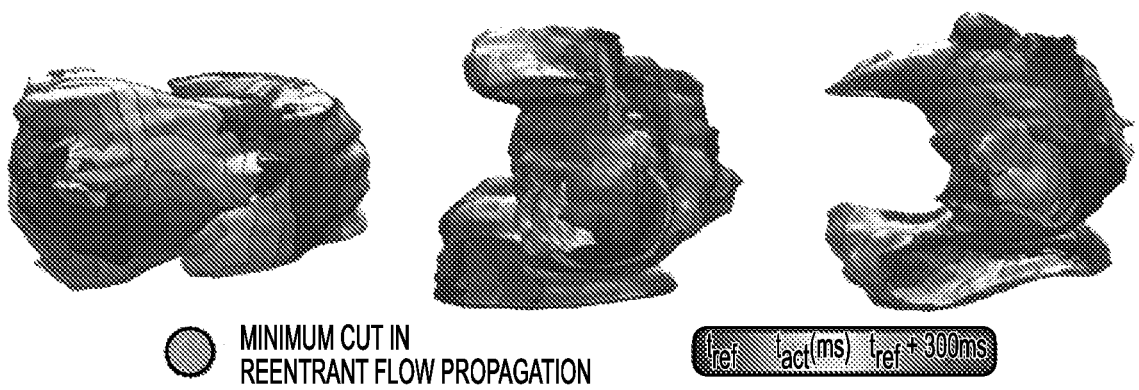
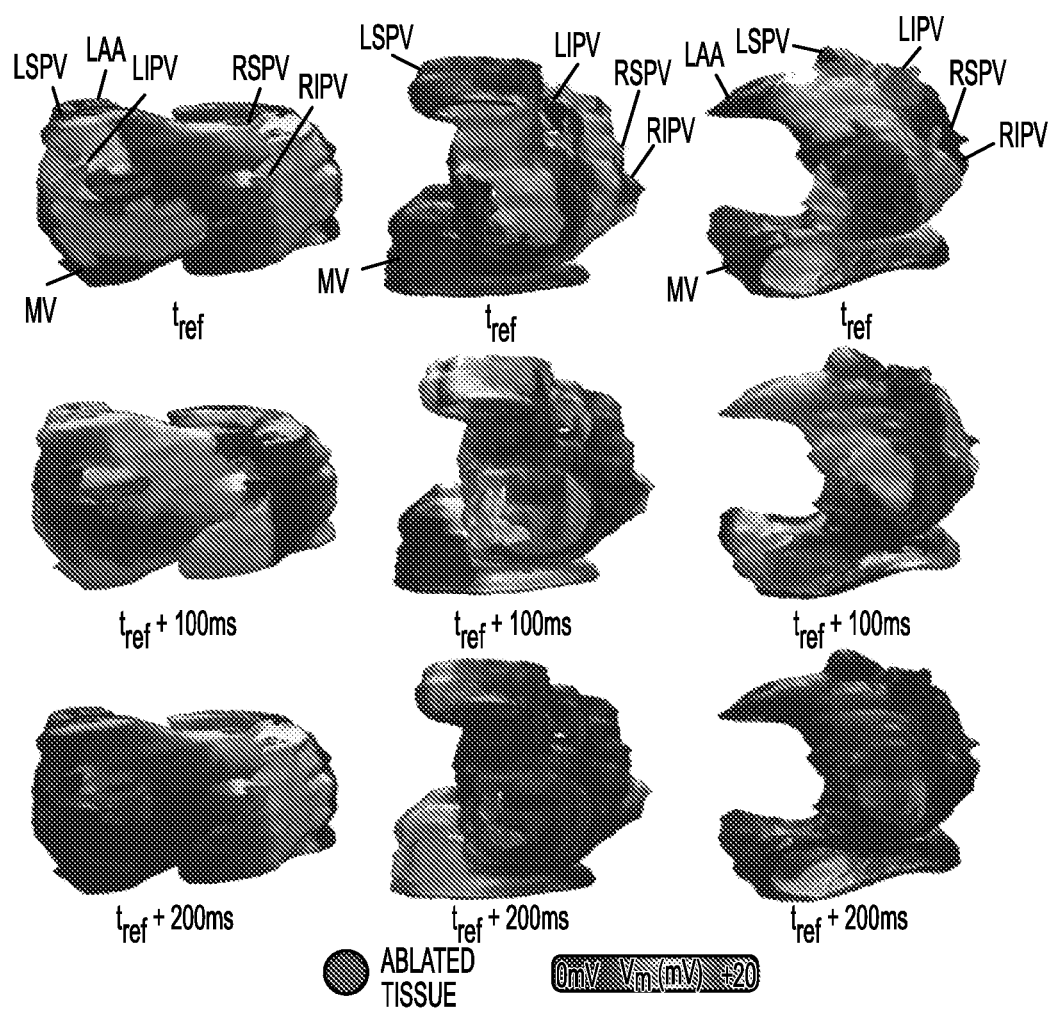
FIG. 14A  FIG. 14B  FIG. 14C
FIG. 14D  FIG. 14E  FIG. 14F

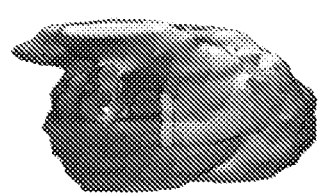
FIG. 15A   FIG. 15B
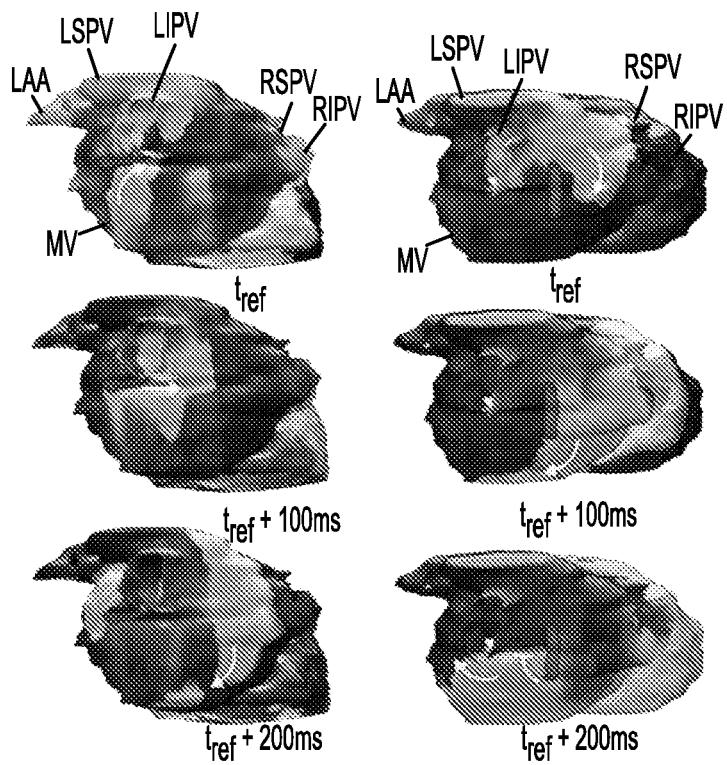
FIG. 15C   FIG. 15D

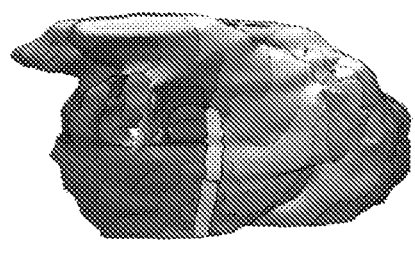
○ BOTTLENECKS IN REENTRANT FLOW
PROPAGATION  ○ PREVIOUS ABLATION
FIG. 16A
$t_{ref}$  $t_{act}$ (ms)  $t_{ref}$ + 400ms
FIG. 16B
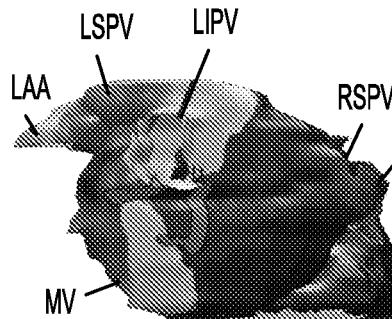
$t_{ref}$
$t_{ref}$ + 100ms
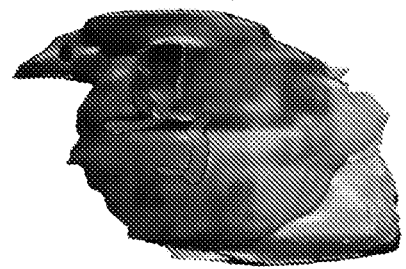
$t_{ref}$ + 200ms
○ ABLATED TISSUE
FIG. 16C
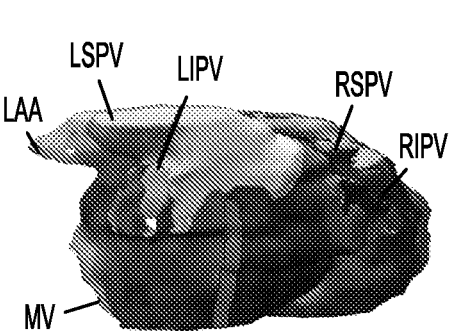
$t_{ref}$
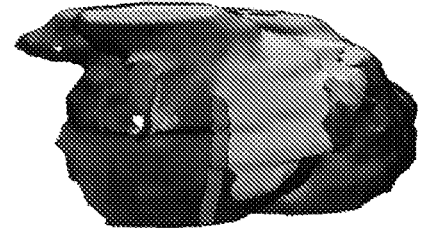
$t_{ref}$ + 100ms
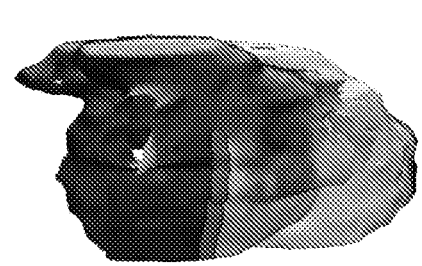
$t_{ref}$ + 200ms
0mV  $V_m$ (mV)  +20
FIG. 16D

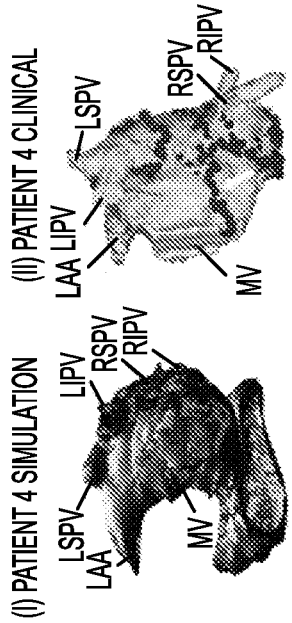 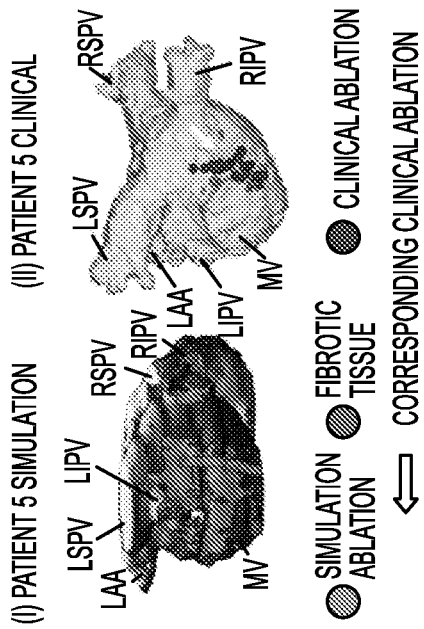 
FIG. 17D
FIG. 17E
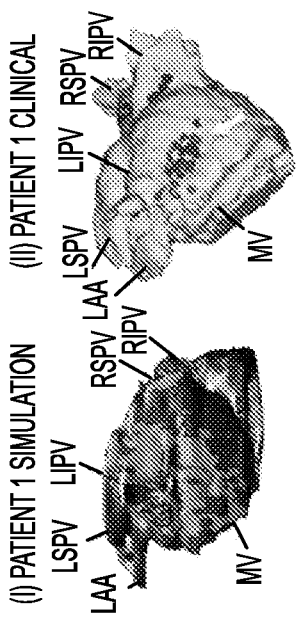 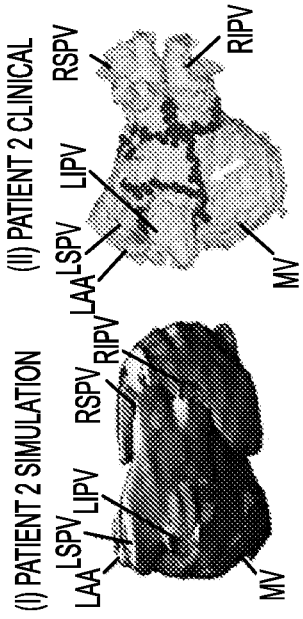 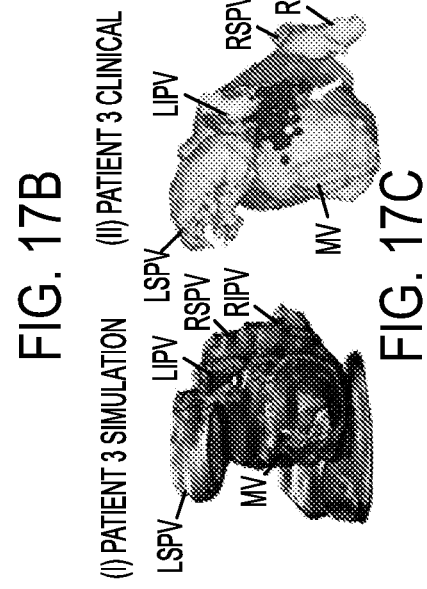
FIG. 17A
FIG. 17B
FIG. 17C

_US 10,842,401 B2_

SYSTEMS AND METHODS FOR SIMULATION PREDICTION OF TARGETS FOR CATHETER ABLATION OF LEFT ATRIAL FLUTTER IN PATIENTS WITH ATRIAL STRUCTURAL REMODELING

CROSS-REFERENCE TO RELATED APPLICATIONS

This application is a 35 U.S.C. § 371 U.S. national entry of International Application PCT/US2016/032219, having an international filing date of May 12, 2016, which claims the benefit of U.S. Provisional Application No. 62/160,518, filed May 12, 2015, the content of each of the aforementioned applications is herein incorporated by reference in their entirety.

FEDERAL FUNDING

This invention was made with government support under grant number HL123271, awarded by the National Institutes of Health. The government has certain rights in the invention.

TECHNICAL FIELD

The present invention relates to systems and methods for simulation prediction of targets for catheter ablation. More specifically, the present invention relates to systems and methods for simulation prediction of targets for catheter ablation of left atrial flutter in patients with atrial structural remodeling.

BACKGROUND

Left atrial flutter (LAFL), a common atrial arrhythmia, typically develops in patients who had prior cardiac surgery or catheter ablation. Anti-arrhythmic drugs are ineffective to treat LAFL, so additional catheter ablation is often used to treat this arrhythmia, but success rates are suboptimal. In LAFL, a reentrant circuit associated with regions of significant structural remodeling (previous ablation lesions, fibrosis or scar) sustains the arrhythmia. Current procedures rely on electro-anatomical mapping to locate the reentrant circuit and ascertain appropriate ablation targets, but this approach is inaccurate, invasive, cumbersome, and time-consuming.

Left atrial flutter (LAFL) is a common form of arrhythmia recurrence in patients following atrial fibrillation (AF) ablation, occurring after up to 31% of AF ablation cases.[75, 76] Sustained by a reentrant circuit in the left atrium, LAFL has an AF equivalent risk of thromboembolic events, is difficult to manage with antiarrhythmic drugs or rate control therapy, and recurs frequently after cardioversion.[76, 77] The preferred strategy to treat this arrhythmia uses catheter ablation to render the critical tissue responsible for sustaining the reentry non-conductive.[78]

Traditional strategies for determining LAFL ablation targets include entrainment and activation mapping during invasive clinical electrophysiology study (EPS).[78] Entrainment mapping uses programmed electrical stimulation to locate the slow conducting zone in the reentrant circuit that perpetuates LAFL.[78] This approach is tedious and can be technically challenging when there are multiple circuits that switch with entrainment maneuvers.[80] Activation mapping plots the time sequence of reentrant wave propagation during LAFL, but this method is encumbered by a time-consuming, non-systematic, point-by-point procedure that requires hundreds of distinct acquisition points.[81] The limitations in these treatment strategies thereby result in long procedure times, which may increase complication rates and fluoroscopy exposure,[80] underscoring the urgent need to develop novel strategies for the identification of the optimal LAFL ablation targets.

SUMMARY

A computer-implemented method for non-invasively identifying ablation locations in atrial tissue, can include: receiving three-dimensional imaging data representing atrial tissue of a left atrial flutter (LAFL) subject, wherein the atrial tissue includes at least one of a left atrium and a right atrium; generating a subject-specific model of the at least one of the atrial tissue from the three-dimensional imaging data; estimating tissue fiber orientations in the atrial tissue; assigning the estimated tissue fiber orientations to the subject-specific model of the atrial tissue; conducting simulations of LAFL using the subject-specific model to identify 1) regions of slow conduction of a propagating wave within an atrial tissue region of the atrial tissue; 2) a critical isthmus of a rotational wavefront within the atrial tissue region; or 3) a region based on a minimum cut in a flow network; and identifying at least one ablation location in the atrial tissue region based on at least one of the identified regions of slow conduction, the critical isthmus, or the minimum cut.

A non-transient computer-readable medium can include computer-executable code that, when executed by a computer, causes the computer to perform: receiving three-dimensional imaging data representing atrial tissue of a left atrial flutter (LAFL) subject, wherein the atrial tissue includes at least one of a left atrium and a right atrium; generating a subject-specific model of the at least one of the atrial tissue from the three-dimensional imaging data; estimating tissue fiber orientations in the atrial tissue; assigning the estimated tissue fiber orientations to the subject-specific model of the atrial tissue; conducting simulations of LAFL using the subject-specific model to identify 1) regions of slow conduction of a propagating wave within an atrial tissue region of the atrial tissue; 2) a critical isthmus of a rotational wavefront within the atrial tissue region; or 3) a region based on a minimum cut in a flow network; and identifying at least one ablation location in the atrial tissue region based on at least one of the identified regions of slow conduction, the critical isthmus, or the minimum cut.

A system can include a computer that comprises a non-transient computer-readable medium comprising computer-executable code that, when executed by the computer, causes the computer to perform: receiving three-dimensional imaging data representing atrial tissue of a left atrial flutter (LAFL) subject, wherein the atrial tissue includes at least one of a left atrium and a right atrium; generating a subject-specific model of the at least one of the atrial tissue from the three-dimensional imaging data; estimating tissue fiber orientations in the atrial tissue; assigning the estimated tissue fiber orientations to the subject-specific model of the atrial tissue; conducting simulations of LAFL using the subject-specific model to identify 1) regions of slow conduction of a propagating wave within an atrial tissue region of the atrial tissue; 2) a critical isthmus of a rotational wavefront within the atrial tissue region; or 3) a region based on a minimum cut in a flow network; and identifying at least one ablation location in the atrial tissue region based on at least one of the identified regions of slow conduction, the critical isthmus, or the minimum cut.

Additional features, advantages, and embodiments of the invention are set forth or apparent from consideration of the following detailed description, drawings and claims. Moreover, it is to be understood that both the foregoing summary of the invention and the following detailed description are examples and intended to provide further explanation without limiting the scope of the invention as claimed.

BRIEF DESCRIPTION OF THE DRAWINGS

Further objectives and advantages will become apparent from a consideration of the description, drawings—which are in color—and examples.

FIG. 13 depicts reentry, minimum cut, and ablation in model #7. (A) Transmembrane maps showing reentry around the mitral valve. (B) Location of minimum cut (cyan) of reentrant flow propagation overlaid on activation map of LAFL episode. (C) Transmembrane maps showing emergence of reentry around the right inferior pulmonary vein after ablation of minimum cut. (D) Location of minimum cut overlaid on activation map of emergent LAFL after ablation. (E) Transmembrane maps showing LAFL termination after in silico ablation was applied (red).

FIGS. 14A-14F depicts locations of minimum cuts in reentrant flow propagation and termination of LAFL by ablation. Location of minimum cuts (cyan) of reentrant flow propagation for model #2 (A), model #3 (B), and model #4 (C) overlaid on activation maps of LAFL episodes. Transmembrane voltage maps showing LAFL termination in model #2 (D), model #3 (E), and model #4 (F) after in silico ablation was applied (red).

FIGS. 15A-15D depict an emergence of post-ablation LAFL. Location of minimum cuts (cyan) of reentrant flow propagation for model #1 (A) and model #5 (B) overlaid on activation maps of LAFL episodes. Transmembrane voltage maps showing emergence of new LAFL in model #1 (C) and model #5 (D) after in silico ablation was applied (red).

FIGS. 16A-16D depict locations of minimum cuts in post-ablation LAFL and termination of arrhythmia by ablation. Location of minimum cuts (cyan) of reentrant flow propagation for model #1 (A) and model #5 (B) overlaid on activation maps of emergent, post-ablation LAFL episodes. Transmembrane voltage maps showing termination of emergent LAFL in model #1 (C) and model #5 (D) after in-silico ablation was applied at minimum cut regions (red).

FIGS. 17A-17E depict comparisons of in silico and clinical ablation targets (those outside of PV isolation lines). Ablated minimum cut in model #1 A:(i), #2 B:(i), #3 C:(i),

4 D:(i), and #5 E:(i). Ablated tissue to terminate LAFL in clinical EPS for patient #1 A:(ii), #2 B:(ii), #3 C:(ii), #4 D:(ii), and #5 E:(ii).

Figure 18A:
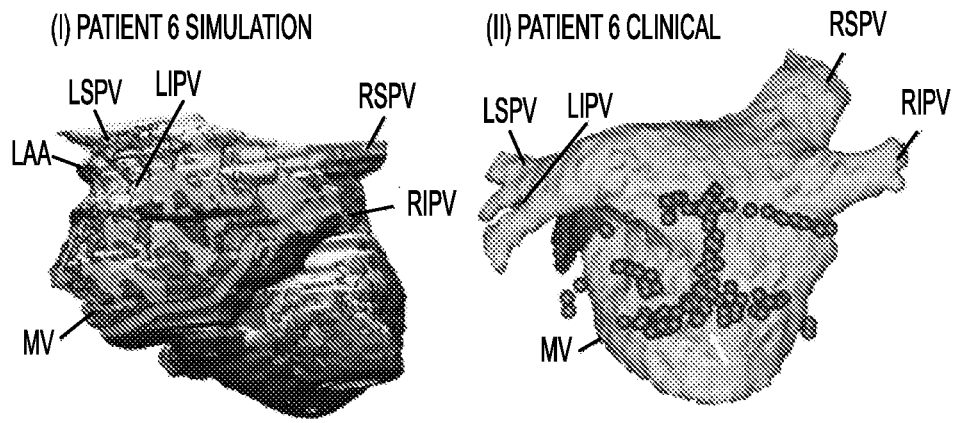
Figure 18B:
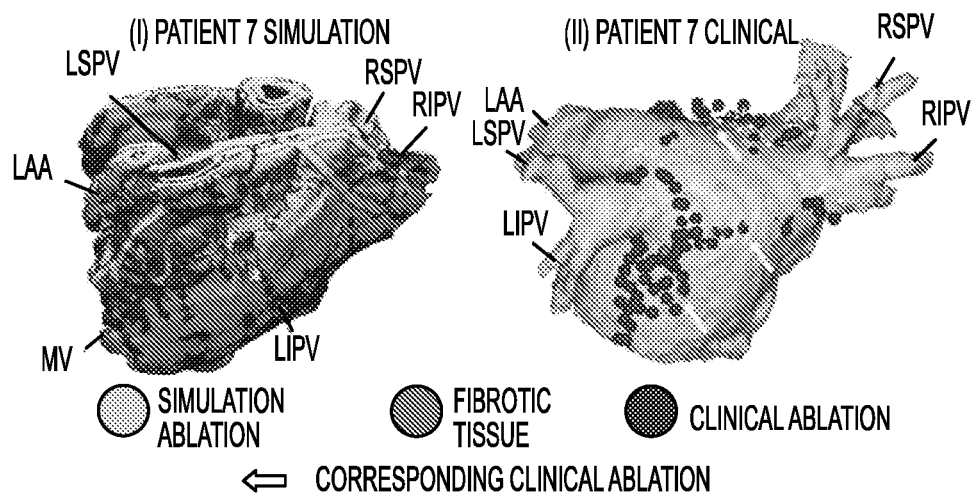

FIGS. 18A-18B depict comparisons of in silico and clinical ablation targets in models 6 and 7. Ablated minimum cut in model #6 A(i), and #7 B(i). Ablated tissue to terminate LAFL in clinical EPS for patients #6 A(ii) and #7 B(ii), as indicated by yellow arrows. Additional ablation lesions were placed in Patient 7 to electrically isolate PVs.

Figure 19A:
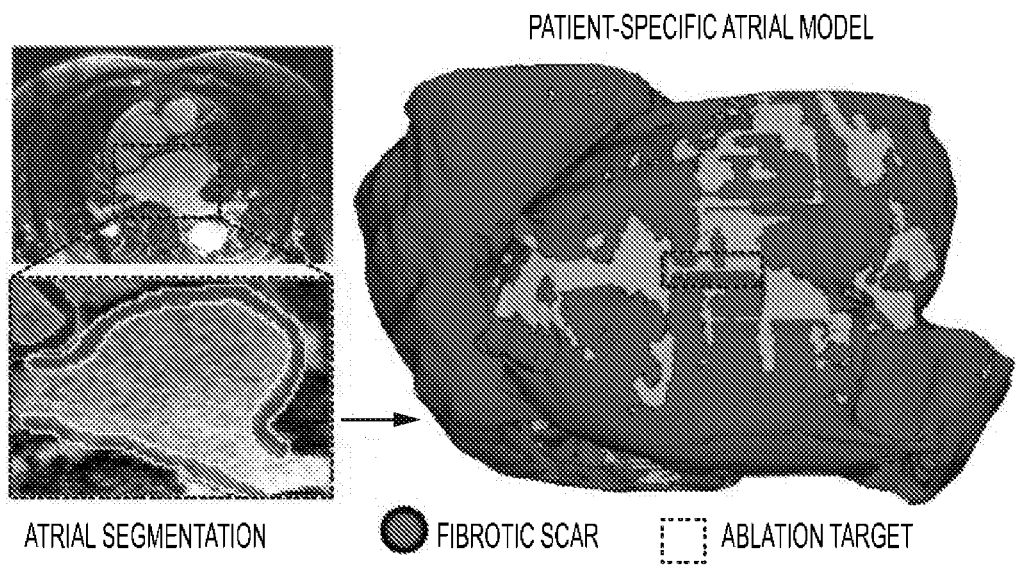
Figures 19B, 19C:
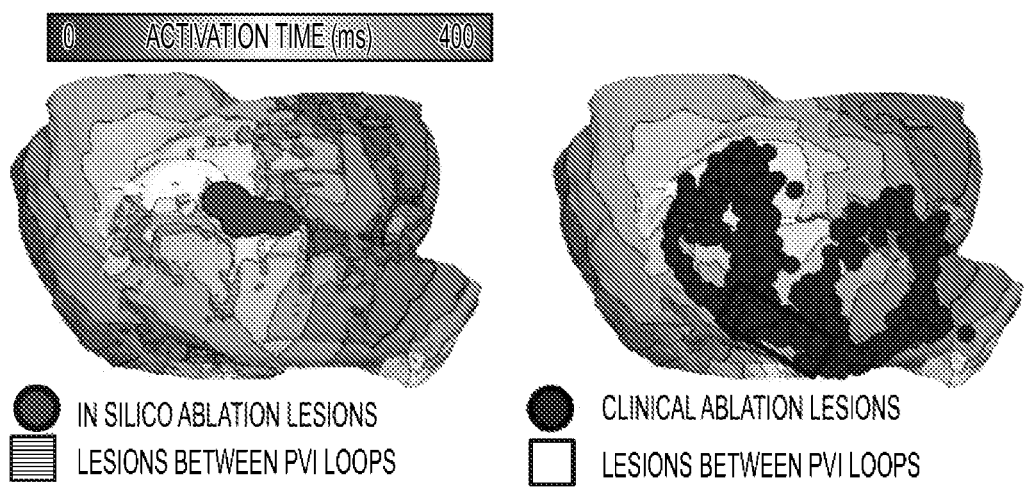

FIG. 19A depicts LGE-MRI data from 7 LAFL patients was used to construct atrial models incorporating scar tissue. In-silico rapid pacing induced LAFL in all patient models. FIG. 19B is an example of in silico ablation sites being compared to lesions delivered during intracardiac electrophysiology study. FIG. 19C shows ablation lines connecting the PV isolation loops to treat LAFL.

Figure 20:

FIG. 20 depicts simulated LAFL in patient-specific models for three patients, characteristics of LAFL in simulations for the three patients, simulated ablation that renders atria non-inducible to LAFL for the three patients, and comparison of simulation findings to clinical findings for the three patients.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference herein in their entireties as if each had been individually incorporated.

Left atrial flutter (LAFL) occurs in patients following cardiac surgery or atrial fibrillation (AF) ablation. Identification of the reentrant circuit (RC) and optimal ablation targets for this arrhythmia remains challenging. Some examples according to embodiments of the current invention test the feasibility of using personalized atrial models incorporating prior scar or structural remodeling to predict optimal LAFL ablation targets.

Some embodiments of the current invention provide a non-invasive methodology for identifying the ablation targets for LAFL in patients with prior structural remodeling. The methodology is an extension of our novel methodology for noninvasive prediction of the optimal ablation targets in patients with atrial fibrillation (AF) and fibrosis disclosed previously and also described in detail below.

Embodiments of the current invention include a method for non-invasively determining the optimal LAFL ablation targets in patients with structural remodeling. Late gadolinium enhancement magnetic resonance imaging (LGE-MRI) is currently used in clinical settings to quantify the extent of atrial structural remodeling (previous ablation lesions, fibrosis, or scar) in each patient. Images from LGE-MRI are used to generate patient-specific computational models that incorporate the patient's unique distribution of atrial structural remodeling. Embodiments of the invention leverage these personalized atrial models as a platform to conduct in-silico simulations capable of identifying the patient's LAFL morphology. From the LAFL morphology, we identify the location(s) of the critical isthmus (region of slow-conducting tissue in the reentrant circuit) and determine the optimal ablation lesions necessary to render the atria non-inducible to LAFL.

As used herein, the term "ablation" is intended to have a broad definition that can include RF ablation, thermal ablation, laser ablation, surgical ablation, cryoablation, and photodynamic therapy, for example.

A computing device may perform certain functions in response to processor executing software instructions contained in a computer-readable medium, such as a memory. In alternative embodiments, hardwired circuitry may be used in place of or in combination with software instructions to implement features consistent with principles of the disclosure. Thus, implementations consistent with principles of the disclosure are not limited to any specific combination of hardware circuitry and software.

Example embodiments may be embodied in many different ways as a software component. For example, it may be a stand-alone software package, a combination of software packages, or it may be a software package incorporated as a "tool" in a larger software product. It may be downloadable from a network, for example, a website, as a stand-alone product or as an add-in package for installation in an existing software application. It may also be available as a client-server software application, or as a web-enabled software application. It may also be embodied as a software package installed on a hardware device.

The following abbreviations and acronyms may be used throughout this disclosure: AF: atrial fibrillation; PV: pulmonary vein; LA: left atrium; LGE-MRI: late gadolinium-enhanced magnetic resonance imaging; VREST: resting membrane potential; APD: action potential duration; IK(Ach): acetylcholine-activated potassium current; Cx: Connexin; LSPV: left superior pulmonary vein; LIPV: left inferior pulmonary vein; RSPV: right superior pulmonary vein; RIPV: right inferior pulmonary vein; and LAA: left atrial appendage.

In our previous patent application (PCT/US2014/068215), the entire content of which is incorporated herein by reference, we described a "method for identifying one or more ablation locations in an atrial tissue region in an atrial fibrillation (AF) patient with atrial fibrosis, the method comprising Receiving three-dimensional imaging data representing the atria of the patient Generating a patient-specific model of the atria from the three dimensional imaging data Conducting simulation of AF using the patient-specific atrial model to identify AF-perpetuating regions; and Identifying from the AF-perpetuating regions one or more ablation locations in the atria"

We determined how the spatial distribution of atrial fibrosis governs AF initiation and maintenance. Specifically, we aimed to demonstrate that virtual electrophysiological study that combines i) the anatomical structure and morphology of the patient atria and the unique distribution of atrial fibrosis as quantified from clinical MRI scans in vivo, and ii) computer modeling of electrophysiology of the atria could be used to predict: (1) how the unique patient-specific atrial fibrosis distribution determines the locations from which ectopic stimuli will degrade into reentrant activity in the fibrotic substrate; (2) the dynamic behavior of persistent AF rotors in the individual atrial substrate; and (3) the optimal locations of ablation of the fibrotic substrate in each patient. To achieve the study goal, we constructed four patient-specific atrial models with distributed fibrosis generated from high-resolution late gadolinium-enhanced magnetic resonance images (LGE-MRI) acquired in vivo from patients suffering from atrial arrhythmias. Fibrotic lesions were modeled with electrophysiological properties that were distinct from non-fibrotic regions; simulations were conducted with dynamic pacing from different, predominantly PV, locations and analysis was performed to determine how fibrotic lesions led to the breakup of pacing-induced wavefronts and their degeneration into reentrant waves, and to the spatial localization of the resulting AF rotors. Finally, simulations were performed to demonstrate that AF could be rendered non-inducible by ablating the fibrotic substrate at locations determined on the basis of knowledge regarding the spatial localization of AF rotors. The simulations may be conducted on the personalized model in order to determine the regions of tissue which maintain the persistent electrical rotors, and ablation lesions may be simulated within these regions to determine the size and shape of the ablation lesion necessary to render the substrate non-inducible to AF. The simulations and analysis may be performed after the LGE-MRI images are captured for the screening process but before an individual undergoes ablation.

The identification of ablation lesions via personalized simulations has the potential to improve outcomes of catheter ablation, shorten the duration of each procedure, and limit the number of repeat procedures.

Methods Used in the PCT/US2014/068215

A group of patients with atrial arrhythmias presenting to the University of Utah for catheter ablation underwent late LGE-MRI acquisition at a resolution of 1250×1250×1500 µm$^3$, following the methodology of Akoum et al[13]. The extent of preablation LA fibrosis was quantified[13], and each patient was stratified into one of four groups: Utah I (<5% LA wall enhancement), Utah II (>5% to <20), Utah III (>20% to <35), or Utah IV (>35). One set of patient data from each of these groups was selected for use in this computational study; the simulations were blinded to the patient history. The amount of LA fibrosis was quantified as 0.8%, 18.0%, 22.8%, and 42.0% for the selected 4 patients from categories Utah I-IV, respectively.

Patient-Specific Modeling

We have recently developed a pipeline for the generation of a 3D patient-specific geometry of the atria with accurate distribution of fibrosis[14]. This pipeline was used here for the creation of the four biophysically detailed fibrotic patient-specific LA models, each from a different Utah category. In this study, we modeled only the LA due to the fact that the clinical correlations drawn. between fibrosis and AF recurrence following ablation were based on quantification of fibrosis in the LA only[10].

FIGS. 1A-1D depict patient-specific distributions of LA fibrosis for substrates Utah I-IV. Briefly, LGE-MRI image segmentation and interpolation was used to produce a high-resolution image of the LA wall with accurate fibrotic lesion distribution for each of the four patients (FIGS. 1A-1D). A finite element tetrahedral mesh was generated from each of the segmented image stacks of the LA,[15] and fiber orientation was estimated as previously described[14,16]. Non-fibrotic regions of the tissue were represented with a modified version of the Courtemanche-Ramirez-Nattel model of the human atrial action potential under AF conditions[17], as described by Krummen et al[18]; the model also included the formulation of the acetylcholine-activated potassium current, $I_{K(Ach)}$, from Kneller et al.[19] Conductivities were chosen such that conduction velocity fell within the range recorded in the human atrium[20], as described in ref[12]. Although this is one way to represent the electrophysiology of the atria, there are many other ways of representing the electrophysiology of the atria, and any of them may also be used with the systems, media, and methods discussed herein.

In our previous study[12] we examined several different representations of fibrotic remodeling in a patient-specific model with extensive fibrosis, generated from a patient suffering persistent AF, to investigate how each mechanistically contributed to AF propensity. In that study we determined that sustained AF resulting from PV pacing matched the AF clinical manifestation when the patient's extensive fibrotic lesions were modeled with a three-component representation of fibrosis, based on experimental evidence. The three aspects of remodeling were: (1) diffuse collagen deposition, (2) gap junction remodeling due to connexin 43 (C×43) protein down-regulation and lateralization, and (3) fibroblast proliferation and phenotype switching into myofibroblasts. Based on our previous findings, we incorporated these three aspects of remodeling into the fibrotic lesions of each of the four patient-specific models in order to determine how the distribution of fibrosis governs the potential degeneration of pacing-induced wavefronts into reentrant circuits as well as the dynamic behavior of the resulting AF rotors.

Diffuse collagen deposition was represented by employing a method of 3D element decoupling to introduce fine conduction barriers along fiber orientation in the fibrotic lesions, as previously described[12,14]. Gap junction down-regulation and lateralization was accounted for, as previously described[12], by altering conductivities to represent the ~30% reduction in C×43 expression in atria in AF compared to sinus rhythm[21], as well as the 3.9-fold higher lateral C×43 labeling in atrial myocytes in AF compared to sinus rhythm[22]. Lastly, myofibroblasts were randomly assigned to 1% of the fibrotic lesions and formed electrical connections with adjacent myocytes, as observed experimentally[23,24]; myofibroblast membrane kinetics were modeled following our previously published methodology[14,25]. Our previous study demonstrated that myofibroblast influences can be equivalently modeled via electrical coupling or paracrine effects[12]. Although this is one way to represent fibrosis, there are many other ways of representing the fibrosis, and any of them may also be used with the systems, media, and methods discussed herein.

Simulation Protocol and Data Analysis

Mathematical description of current flow was based on the monodomain representation of the myocardium and simulations were executed using the simulation package CARP (CardioSolv LLC)[26]. To investigate how the distribution of fibrosis determines whether dynamic pacing will degrade into reentrant activity and initiate AF, ten pacing locations were chosen in each substrate to represent ectopic triggers. Stimulus locations were distributed around the PVs (where most ectopic beats originate[3]) such that five stimuli were located within the left PVs (stimuli L1-L5 in each LA model, FIGS. 1A-1D) and five were located within the right PVs (stimuli R1-R5 in each LA model, FIGS. 1A-1D). Specifically, two pacing sites were located on opposing sites of each PV, one site was located between the left PVs, and one site was located on opposing sides of each PVs. For each pacing location, a dynamite pacing protocol was used to assess arrhythmia inducibility, as performed clinically.[8] The protocol consisted of pacing for 5 beats at a 365 ms, cycle length, followed by two boats in cycle lengths of each of the following 290 ms, 285 ms, 280 ms, 275 ms, 270, 268 ms, 266 ms, 264 ms, 262 ms, and 260 ms. Sustained AF was defined as fibrillatory activity lasting for 10 seconds after the delivery of the last stimulus. Additional stimuli were placed as necessitated by initial simulation results.

In order to investigate how patient-specific distributions of atrial fibrosis govern AF initiation and maintenance, the following analysis was performed.

To determine if simulations using the patient-specific models could accurately represent the ability of an LA substrate to support AF, the simulations were performed blinded to patient history. Substrates in which stimuli from one of more locations initiation AF were considered susceptible to AF. Predictions were considered accurate if the simulation outcomes (susceptible vs. not susceptible to AF) accurately matched the patient's clinical history.

To asses the influence of fibrotic lesion distribution on AF inducibility from different PV pacing locations, the distance between each stimulus site and its closest fibrotic lesion was calculated in substrate in which AF was observed.

Identifying Rotors and Representing Ablation

In models inn which AGF resulted from PV pacing, phase singularities (rotor organizing centers) were calculated over a period of 10 seconds, and the phase singularity meander quantified for each rotor. Ablation lesions were implemented in the models to target the regions of tissue which maintained the persistent phase singularities. Lesions were modeled as one or more transmural regions[31] of inexcitable tissue, they were circular to account for catheter tip shape, and 7 mm in diameter (within the range of clinical ablation lesions[8]). Arrhythmia inducibility was tested after the implementation of each ablation lesion until AF could no longer be initiated following dynamic pacing.

Results of PCT/US2014/068215

Arrhythmia Inducibility in Patient-Specific Models

Figure 1D:
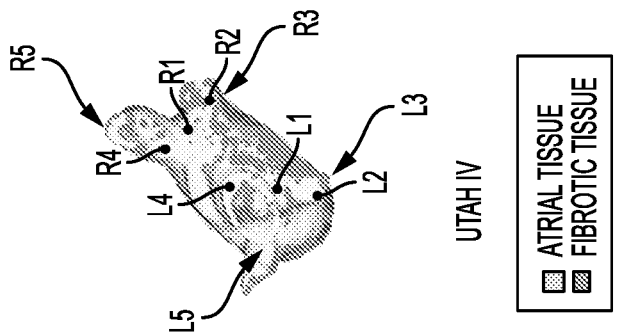
FIGS. 1A-1D depict patient-specific distributions of LA fibrosis for four patients. Each of these four patients had an amount of left atrial (LA) wall MRI enhancement (i.e. amount of atrial fibrosis) belonging to one of four groups: Utah I (≤5%), Utah II (>5% to ≤20), Utah III (>20% to ≤35), or Utah IV (>35); the amount of LA fibrosis in the four chosen patients was thus quantified as 0.8%, 18.0%, 22.8%, and 42.0%. Pacing locations in the left pulmonary veins (PVs) (L1-LS) and right PVs (R1-RS) are indicated for each reconstructed patient-specific atrial model in FIGS. 1A-1D. Anatomical locations for the left superior PV (LSPV), left inferior PV (LIPV), right superior PV (RSPV), right inferior PV (RIPV), and LA appendage (LAA) are indicated in FIG. 1A; all models in FIGS. 1A-1D are presented in identical orientations.
Figure 1C:
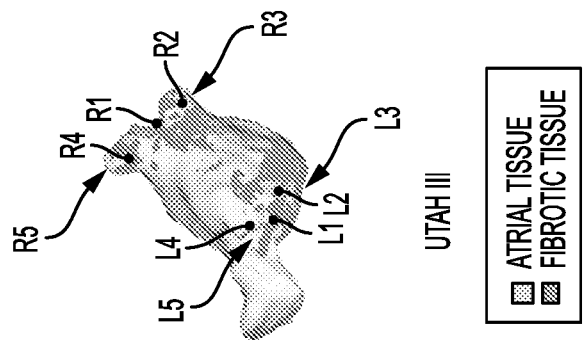
Figure 1B:
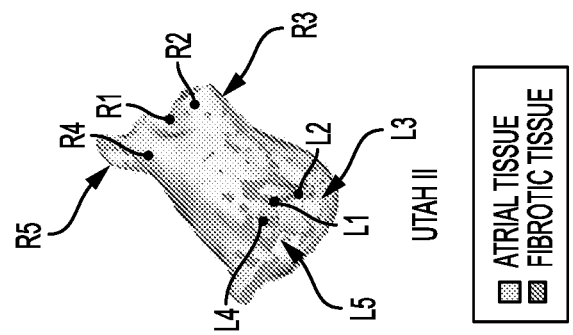
Figure 1A:
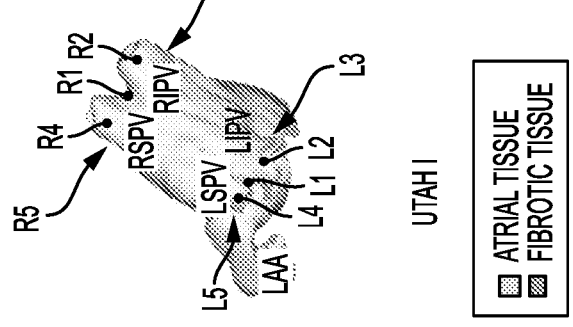

Substrate propensity to AF was initially tested from the ten PV locations in each of the four patient-specific models of the fibrotic LA. Neither the Utah I nor the Utah II substrates gave rise to arrhythmia following pacing from any of the ten locations. The Utah III substrate gave rise to sustained AF following pacing from two of the ten pacing locations; those were pacing sites L2 and L4 (as marked in FIG. 1C). Pacing from three of the ten PV locations (L1, L4, and R1, as seen in FIG. 1D) resulted in sustained AF in the Utah IV substrate.

Figure 2:
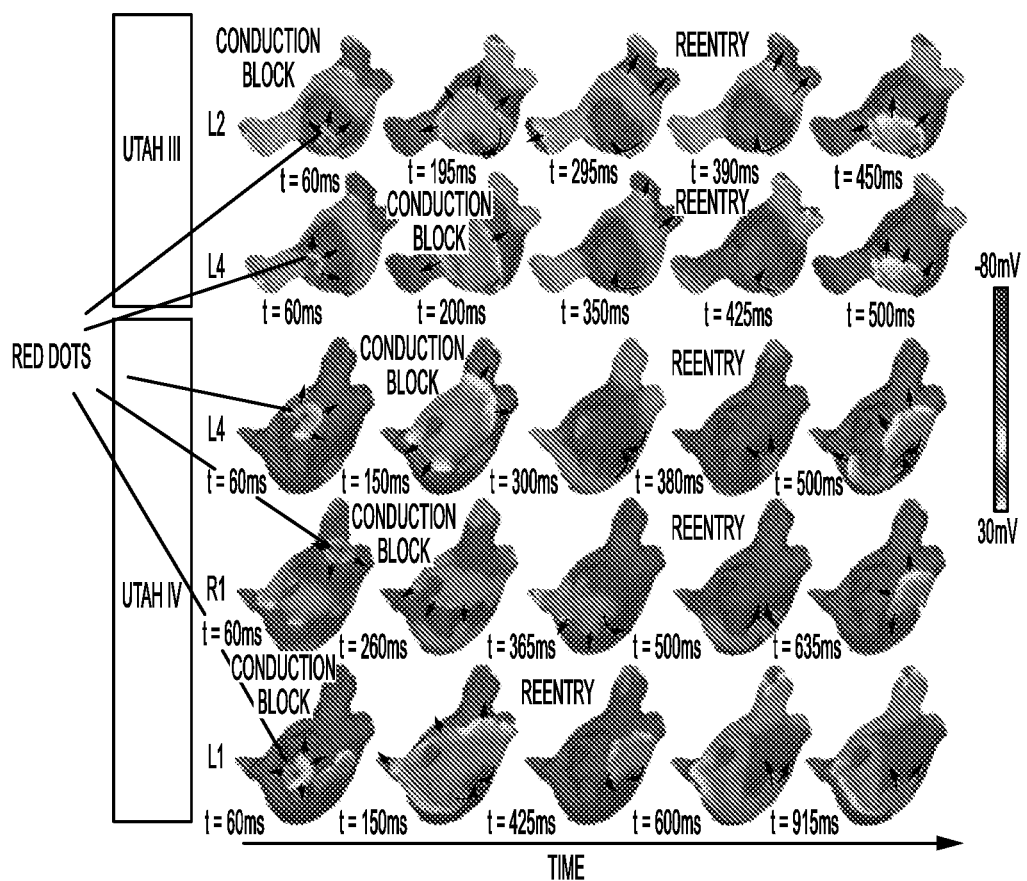
FIG. 2 depicts transmembrane potential maps at five time instants, documenting AF initiation in substrates Utah III (top two rows) and Utah IV (bottom three rows) from different PV pacing locations (as noted at left). Lines of block are marked in red. White arrows indicate direction of propagation. Darker areas (left-most column) indicate pacing location.

FIG. 2 presents the events leading to the formation of the first cycle of reentry resulting from dynamic pacing at locations that initiated AF in substrates Utah III and Utah IV. In each case, unidirectional conduction block (as denoted by the red lines in FIG. 2) took place. It resulted from either the stimulus-induced wavefront encountering tissue in a refractory state (Utah IV: R1) or the collision of the stimulus-induced wavefront with the wavefront that was the result of the preceding beat from the pacing protocol (Utah III: L2 and L4; Utah IV: L1 and L4). The latter case was possible because of the slow and discontinuous conduction that occurred in the large fibrotic lesions in substrates Utah III and Utah IV, resulting in the wave taking a propagation direction different from that in nonfibrotic tissue. Following unidirectional conduction block in substrates Utah III and Utah IV, a reentrant circuit was formed, marking AF onset.

After the computational study was complete, patient history was provided to our team. In all substrates, simulation outcomes faithfully represented the patient clinical manifestation. The patients from which the Utah I and II LA models were generated did not suffer from AF, while the patients whose scans were used to create the Utah III and IV LA models both suffered from AF.

Distribution of Atrial Fibrosis Determines Whether Paced Beats Degrade Into AF

The results from our simulations revealed that all stimuli of the dynamic pacing protocol were delivered in all cases in which AF was initiated (i.e., in these cases the dynamic pacing protocol, which consisted of pacing starting at cycle lengths of 365 ms and proceeding down to 260 ms, resulted in reentry formation). In most cases in which AF was not initiated by pacing from a given PV site in substrates Utah III and IV, a stimulus from the pacing train failed to excite tissue and pacing-induced propagation thus failed before the pacing protocol was completed (that is, prior to reaching cycle lengths of 260 ms). The observation that AF ensued only after propagation was elicited following the shortest pacing cycle lengths in the dynamic pacing protocol is consistent with experimental findings that show short effective refractory periods are significantly correlated with an increased probability of sustained AF[27].

We have previously demonstrated that the electrophysiological effects of fibrosis in the atria extends beyond the borders of fibrotic lesions themselves, well into non-fibrotic tissue[12]. Indeed, APD changes occur in non-fibrotic tissue due to influences from nearby fibrosis; the extent of APD changes attenuates with the distance from the fibrotic lesion[25]. Therefore, given that repolarization dynamics throughout the LA are altered non-uniformly by fibrosis, in a distance-to-fibrotic-region-dependent manner, we sought to determine how a PV pacing location's distance to the region of fibrosis affects the ability of a stimulus from that location to elicit excitation in the LA in the Utah III and IV models. To perform this analysis, the distance between each PV pacing site and its closest fibrotic lesion was plotted against the pacing cycle length of the stimulus from that location's pacing train that failed to elicit excitation in substrates Utah III and IV.

Figure 3:
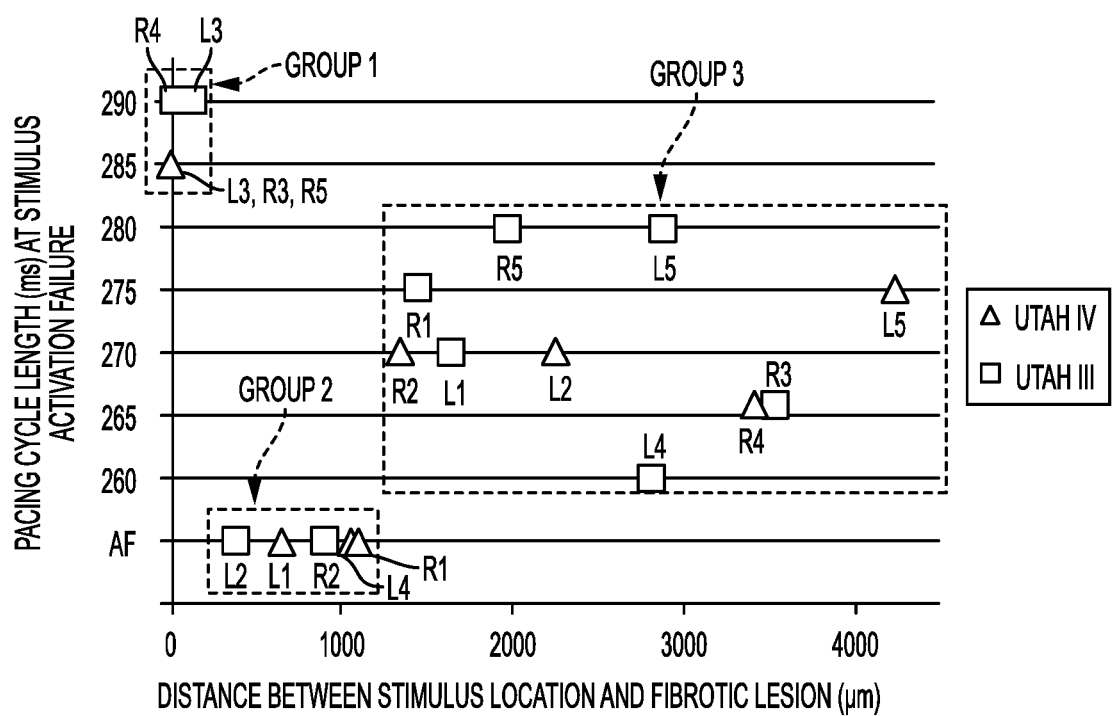
FIG. 3 depicts a plot of the distance between each pacing site and its closest fibrotic lesion vs. the pacing cycle length at which a stimulus either failed to excite the tissue or resulted in AF in substrates Utah III (red squares) and Utah IV (blue triangles). Stimulus locations are labeled for each data point. Groups 1-3 are indicated for discussion purposes.

Results are presented in FIG. 3. In cases when AF was initiated, the cycle length is 260 ms, the shortest cycle length in the pacing protocol. The graph demonstrates a clustering of three groups of data points: Group 1, PV pacing locations for which there was a fibrotic lesion in close proximity (<120 µm) and for which stimuli with cycle lengths of 285-290 ms in the pacing protocol failed to excite the tissue; Group 2, PV pacing locations that were between 378 and 1052 µm from fibrotic lesions and for which sustained AF resulted following the execution of the entire dynamic pacing protocol; and Group 3, stimulus locations that were far from fibrotic lesions (>1330 µm) and for which stimuli with cycle lengths of 260-280 ms failed to excite the tissue.

Based on the finding that stimuli that are located at a distance between 378 and 1052 µm from fibrotic lesions can initiate AF in models Utah III and IV, the distance between each point in the non-fibrotic tissue and the closest fibrotic lesion was calculated to determine what locations would fall within the range of "sweet spot" distances to fibrotic lesions and could therefore be considered "prime ectopic spots" for AF initiation. We found that "prime" locations comprise 3.56% and 4.43% of LA volume (including the PVs) in the Utah III and IV models, respectively. A disproportionately large amount of this "prime" tissue was localized in the PVs, 19.78% and 32.56% in the Utah III and IV substrates, respectively, although the PVs comprised only 14.9% and 22.93% of total tissue volume, respectively, in these models. Building on this finding, pacing trains were delivered from two locations in "prime" tissue outside of the PV regions in substrates Utah III and IV to test AF inducibility; consistent with our predictions above, sustained AF was initiated by pacing from these locations following the dynamic protocol (data not shown).

Distribution of Atrial Fibrosis Determines AF Rotor Location

Figure 4:
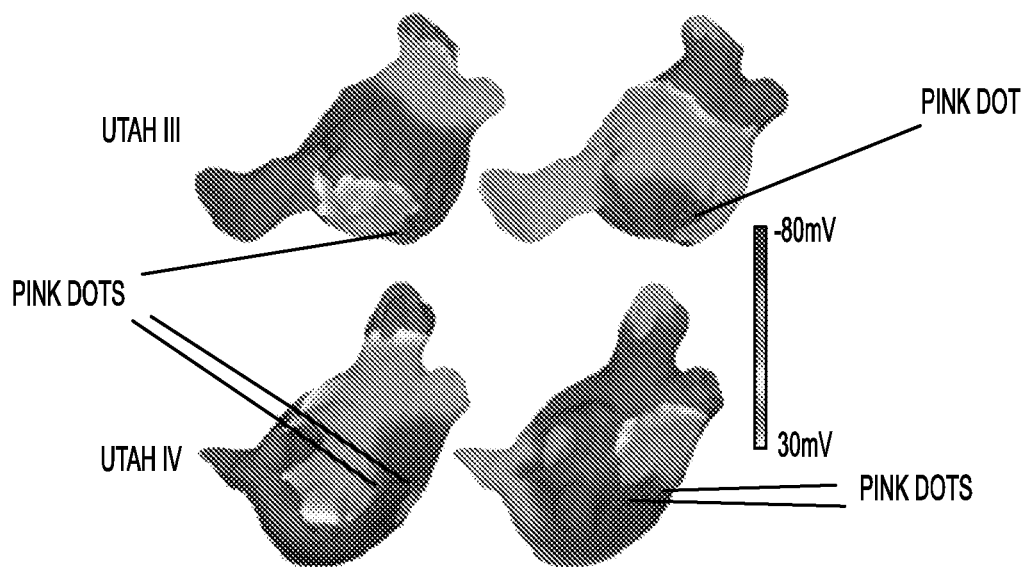
FIG. 4 depicts transmembrane potential maps at two time instants in substrates Utah III (top row) and Utah IV (bottom row) demonstrating the meandering of the mother rotor organizing centers termed phase singularities (shaded areas). Regions of meander are outlined with dashed lines.

Epicardial phase singularities were calculated in all of the cases in which pacing resulted in AF initiation. Phase singularities, as opposed to filaments, were examined due to the fact that the walls of the LA are thin (<3 mm) as well as for ease of analyzing the meandering of the rotor organizing centers over time in our models. In the Utah III and IV models AF was characterized with the formation of one or more mother rotors, which persisted for the duration of the AF simulations, as well as other "breakoff" fibrillatory activity, the phase singularities of which appeared and vanished quickly. Once AF was initiated, the phase singularities associated with the persistent reentries meandered within the same tissue regions in each substrate, regardless of the pacing location from which AF was induced, indicating that the patient-specific distribution of fibrosis, rather than the location of atrial trigger, was the most important factor governing AF mother rotor location(s). In the Utah III substrate, one persistent (mother rotor) phase singularity was found to meander within an approximately oval region of tissue with long and short diameters of 13.2 mm and 6.7 mm, respectively (FIG. 4, top row; mother rotor phase singularities locations at the given instant of time are shown by the pink dots; regions of meander are outlined by red dashed line). In the Utah IV substrate, there were two persistent phase singularities, one meandering within a larger oval region of tissue with long and short diameters of 13.7 mm and 6.2 mm, respectively, and one meandering in a smaller approximately circular region of tissue that was 6.6 mm in diameter (FIG. 4, bottom row).

Figure 5:
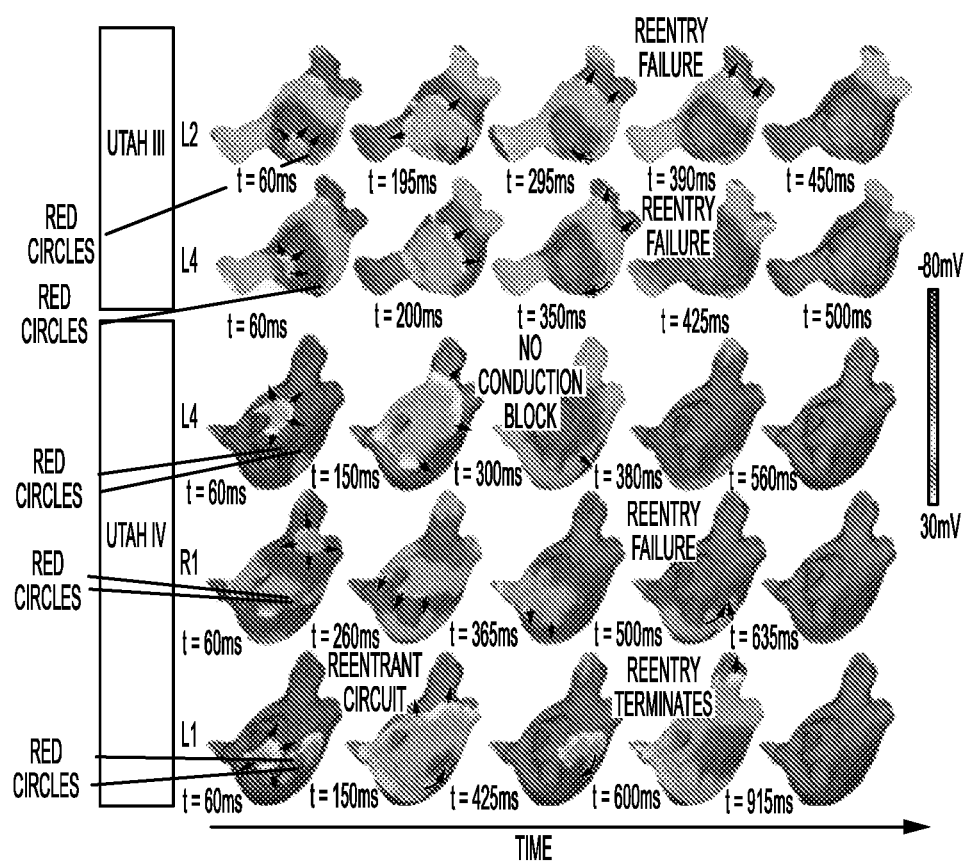
FIG. 5 depicts transmembrane potential maps at five time instants in substrates Utah III (top two rows) and Utah IV (bottom three rows) from different pacing locations (as noted at left) with ablation lesions modeled. Red circles (as indicated in the figure and in left-most column) indicate the extent of ablation lesions. White arrows indicate direction of propagation. Time instances and pacing locations are identical to those presented in FIG. 2.

Ablation was applied, as described in Methods, to regions within which the persistent (mother rotor) phase singularities (which are the rotor organizing centers) meandered. Snapshots of transmembrane potential distributions at time instants throughout simulations with ablation lesions modeled are shown in FIG. 5; the selected time instants are identical to those presented in FIG. 2 to allow for comparison. The implementation of ablation consisting of two overlapping circular lesions (indicated in red in the left-most images in FIG. 5), fully covering the long diameter (13.2 mm) of the region of mother rotor phase singularity meander was necessary to result in AF non-inducibility in the Utah III substrate following pacing train delivery from both the L2 and L4 locations. In the Utah IV substrate, two separate ablations were implemented to render inexcitable the regions of meander of the two persistent phase singularities. The smaller region of meander was targeted with one circular ablation, while the larger region of meander was targeted with two overlapping circular lesions to again fully cover the long diameter of the region of persistent phase singularity meander (13.7 mm). The ablations (indicated in red in the left-most substrates in FIG. 5) resulted in AF non-inducibility following pacing from all three original locations (L1, L4, and R4) in the Utah IV substrate. It was not possible to achieve AF non-inducibility with fewer or smaller ablation lesions.

Discussion of PCT/US2014/068215

This study demonstrates the feasibility of using a patient-specific simulation approach to predict the role of the unique atrial fibrotic distribution in the dynamics of the patient's persistent AF. The study elucidated how patient-specific fibrosis distribution determines whether ectopic stimuli result in persistent AF, and from which specific atrial locations. We evaluated the dynamic behavior of persistent AF rotors in the patient atria; based on this analysis, and particularly, on the predicted spatial localization of persistent AF rotors, we performed feasibility simulations showing that AF could be rendered non-inducible, in a patient-specific approach, by ablating regions of persistent rotor meander in the fibrotic substrate. The present study has, thus, two contributions, each discussed below: one in mechanistic understanding of the role of the fibrotic substrate in persistent AF, and another, in demonstrating that it is feasible to identify the optimal targets of atrial ablation in the patient using the approach presented here prior to the clinical procedure. The main mechanistic findings in this study are:

(1) The mechanisms which determine whether pacing from a given atrial site will degrade into AF, operate in a distance-to-fibrosis-dependent fashion, with pacing from locations only in the mid-range of distances (378-1052 µm) to fibrotic lesions resulting in sustained AF.

(2) A disproportionate amount of all non-fibrotic tissue that falls in the mid-range (i.e., arrhythmogenic "sweet spot") distance to fibrotic lesions is located in the PVs.

(3) Patient-specific distribution of fibrosis, rather than location of pacing (i.e. location of arrhythmia trigger), governs AF "mother rotor" location(s) and meander; phase singularities associated with persistent reentries meander within the same tissue regions once AF is initiated, regardless of the pacing location.

In this study, two out of ten PV stimulus locations resulted in AF initiation in the Utah III substrate (with 22.8% fibrosis), while three out of ten PV stimulus locations caused AF in the Utah IV substrate (with 42.0% fibrosis); no PV stimuli caused AF in the Utah I and II models. This finding demonstrates a correlation between the amount of fibrosis and the probability of a trigger initiating AF; it is consistent with the correlation found between AF incidence and percent fibrosis in the LA[9], the underlying cause of which has remained unknown. Our study findings suggest a new paradigm, that AF incidence may be higher in patients with more fibrosis due to the fact that larger degrees of fibrosis cause locations in the substrate to become "prime" for triggering AF. Indeed, we demonstrated that "prime" trigger locations comprise 3.56% and 4.43% of the Utah III and IV substrates by volume, respectively, of which disproportionate amounts were located in the PVs. The concept that ablation may eliminate "prime" tissue may help explain the perplexing clinical finding that triggered activity, which can remain frequent years after linear LA ablation, often does not initiate AF[37]. Should linear LA ablation eliminate "prime" tissue itself or create an electrical barrier that prevents fibrotic lesions from altering nearby tissue electrophysiology, such that "prime" regions are not created, substrates could be rendered noninducible to AF, despite the presence of triggered activity.

Traditionally, AF treatments have either been aimed at suppressing atrial triggers that initiate AF[4], or at modifying the substrate that sustains it[6,7]. In this study, however, the spatial distribution of atrial fibrosis was found both to determine whether pacing initiates AF and to govern the dynamics of the resulting AF rotors. The fact that the distribution of atrial fibrosis modulates both AF initiation and its maintenance creates a new paradigm for AF treatment, in which one treatment strategy could possibly target both AF-triggering and -perpetuating mechanisms. Indeed, this study demonstrated that in all cases when the regions of meander of persistent phase singularities were ablated, reentrant circuits could not form following pacing from locations that had previously resulted in sustained AF (FIG. 5). This concept may explain why a novel ablation strategy, aimed at ablating AF electrical rotors, has reported a higher degree of successful patient outcomes as compared to PV electrical isolation[8]. Consistent with our finding that the implementation of 1 to 2 ablation lesions led to AF non-inducibility, Narayan et al. reported that an average of 2.1±1.0 electrical rotors were observed in patients with sustained AF, and that the ablation of these rotors led to successful termination of AF[8].

This study was conducted without knowledge of the history of the patients the scans of whom were used to create the models; the simulations accurately predicted the clinical outcome of each of the four patients. Indeed, models which resulted in AF (Utah III and IV) turned out to have been generated from patients suffering AF, while models which did not result in AF (Utah I and II), turned out to have been derived from AF-free patients. Our proof-of-concept simulations thus indicate that patient-specific modeling of atrial arrhythmogenesis under fibrotic conditions could become in the future a powerful new non-invasive tool to stratify atrial arrhythmia risk.

In this study we demonstrated that a virtual electrophysiological study using patient-specific atrial models could provide a novel way to identify regions of meander of persistent (mother rotor) phase singularities based on the individual spatial distribution of fibrosis. We showed that ablating these regions of meander in the models results in AF non-inducibility from any stimulus location. This study therefore presents the proof-of-concept of a non-invasive approach to the identification of the ablation targets for persistent AF in the fibrotic atria. In its translation to the clinic, we envision that the approach will entail the use, prior to the clinical procedure, of an MRI-based subject-specific multiscale electrophysiological model of the fibrotic atria to analyze AF dynamics and rotor meander, and to determine the targets of ablation. Once the targets of ablation are determined and visualized by the present approach, we envision that ablation delivery for AF termination could be swift and precise, eradicating, with a minimal number of lesions, all rotors in the fibrotic substrate. This could dramatically improve the efficacy of ablation, increase the tolerance for the procedure, and reduce post-procedure complications and long-term deleterious effects resulting from the lengthy invasive mapping and the numerous unnecessary ablation lesions.

Study Limitations of PCT/US2014/068215

Because fibrosis was identified in the LA only, for computational tractability, simulations used only the LA to determine AF rotor dynamics and perform ablation. The methodology would not change when modeling both atria; similarly, the insights obtained here will remain the same. With additional fibrosis in the RA, persistent rotors might meander in the RA, necessitating ablation lesions there as well. Another limitation of the study is the small number of patient scans due to the low resolution of the scans. However, image resolution is likely to improve with time and advances in MRI technology, which will improve the utility of our approach.

Funding Sources of PCT/US2014/068215

The authors gratefully acknowledge support of this work by the American Heart Association Predoctoral Fellowship to K.M and the National Institutes of Health (grants HL103428 and HL105216) to N.T. This work was also supported in part by the U.S. National Science Foundation, grant NSF-OCI-108849. We also acknowledge support for image processing and model generation software from the Center for Integrative Biomedical Computing (CIBC) at the University of Utah, sponsored by NIH Grant P41 GM103545-14.

In embodiments of the present invention, we also receive three-dimensional data representing the atria of the patient and generate a model of the patient's atria from imaging. However, in embodiments of the present invention, we conduct simulations of another arrhythmia, LAFL. Further, we previously identified the optimal ablation targets based on the locations of AF-perpetuation regions, while in embodiments of this invention we identify optimal ablation lesions based on the location of the zones of slow conduction or the critical isthmus, and then extending the lesion to an electrically non-conductive region or another lesion, or based on minimum cut in a flow network as described below.

EXAMPLES OF EMBODIMENTS OF THE PRESENT INVENTION

Methods of Embodiments of the Present Invention

Study Population

This study included patients with LAFL who received a pre-procedural LGE-CMR scan between April 2012 and March 2014. Exclusion criteria included previous cryoballoon or laser ablation, LAFL during CMR acquisition, or suboptimal LGE-CMR scan quality, resulting in a total of 10 patients for this study. The Johns Hopkins Institutional Review Board approved the study, and all patients provided informed consent.

Construction of Patient-Specific Atrial Models

Patients with LAFL underwent an LGE-CMR evaluation on a 1.5-Tesla magnetic resonance scanner (Magnetom Avanto and Aera, Siemens Medical Systems, Erlangen, Germany). Vertical and horizontal long-axis cine, LGE-CMR images FIG. 6, I.A) were acquired at a resolution of 1.5×1.5×2.0 mm according to the methodology of Khurram et al.[39,40] After the right and left atrial walls were manually contoured in Seg3D[41] (University of Utah Center for Biomedical Computing, Utah, USA), fibrotic and non-fibrotic tissue regions were segmented (FIG. 6 I.B) using an image intensity ratio (IIR) algorithm implemented in Matlab (Mathworks, Nattick, Mass., USA). This algorithm calculated the ratio of the voxel intensities at every point in the atrial wall to the mean voxel intensity of the left atrial blood pool. Voxels with an IIR above 0.97 were selected to correspond to fibrotic tissue since voxels in this IIR range most accurately correlated to atrial tissue with bipolar voltage less than 0.5 mV,[39] an indicator of fibrotic myocardium.[42] After the segmented images were up-sampled to an isotropic voxel size of 400 µm3 via shape-based interpolation,[43] 3D finite-element tetrahedral meshes were generated (FIG. 6 I.C) from the resulting high-resolution data set[44] and atrial fiber orientations were assigned (FIG. 6, I.D) using a rule-based method.[45] In some embodiments, fiber orientations can be estimated and then be assigned. However, in some embodiments LAFL simulations can be done without fibers but with just fibrotic/non-fibrotic regions and anatomical geometry. The fiber orientations, the fibrotic/non-fibrotic regions and the anatomical geometry can be used as geometric modifications to the subject-specific model. Thus, embodiments of the invention can include estimating tissue fiber orientations in the atrial tissue and assigning geometrical modifications to the subject-specific model, where the geometric modifications include the estimated tissue fiber orientations. An in-depth description of the methods for reconstructing atrial models is available in our previous publications.[46-48]

Modeling of Atrial Electrophysiology

Non-Fibrotic Tissue Representation:

Membrane kinetics of myocytes in non-fibrotic tissue regions were represented with the Courtemanche-Ramirez-Nattel (CRN) model of the human atrial action potentia[49,50] modified to fit intracardiac data in patients ((FIG. 6, I.E, gray).[51] At the tissue level, conductivity values were selected to achieve a longitudinal conduction velocity (CV) of 43.49 cm/s in the non-fibrotic myocardium, which was within the range of CV values recorded in patients with atrial flutter.[52]

Fibrotic Tissue Representation:

To account for the electrophysiological consequences of fibrotic remodeling,[53-57] membrane kinetics of myocytes in fibrotic regions were represented with a modified CRN model (FIG. 6, I.E, green), incorporating a 50% reduction in inward rectifier potassium current, 50% reduction in L-type calcium current, and 40% reduction in sodium current. These modifications are based on documented changes in atrial myocytes' electrophysiology when subjected to increased expression of transforming growth factor β1, a key promoter of the fibrogenic signaling pathway.[58-60] Compared to those of myocytes in non-fibrotic tissue regions, the action potentials of myocytes in fibrotic regions had a 15.4% increase in duration, 7.18% elevation in resting transmembrane voltage, and 49.6% decrease in upstroke velocity. These ionic current changes were consistent with the action potential alterations documented in experimental studies of fibrotic myocardium.[61]

To account for the decreased intercellular coupling due to replacement fibrosis, interstitial fibrosis, and gap junction remodeling in fibrotic regions,[62-65] longitudinal conductivity values in fibrotic regions were reduced by 30% compared to those in non-fibrotic regions. Because fibrosis results in greater CV impairment in the direction transverse to cardiac fibers, the transverse conductivity values were further modified to achieve a longitudinal-transverse anisotropy ratio of 8:1.[62, 65]

Clinical Electrophysiology Study and Ablation

In the clinical ablation of LAFL, each patient underwent standard EPS under the guidance of a 3D electroanatomical mapping system (CARTO, Biosense Webster, Diamond Bar, Calif.). Programmed stimulation was performed in order to induce LAFL. The ablation catheter (Thermocool, Biosense Webster) was introduced into the left atrium by a transseptal approach via a femoral vein. A critical isthmus, or a central common pathway, of the LAFL reentrant circuit was identified by entrainment mapping, where a match of the tachycardia cycle length to the post pacing interval (time interval between pacing site and onset of P wave) was achieved. Radiofrequency ablation energy of 30 W using 4 mm tip irrigated catheters was delivered at sites in the central common pathway. To prevent LAFL recurrence, additional lesions were executed to modify the atrial substrate, where the exit sites of the central common pathway were also ablated. If reconnected pulmonary veins (PVs) were observed, additional lesions were applied to achieve PV isolation. After ablation, programmed stimulation was repeated. Acute success was defined as the inability to induce clinical LAFL at the end of the procedure.

Simulation Protocol

Electrical wave propagation was governed by the monodomain formulation. Finite-element simulations were executed with the CARP software package (Johns Hopkins University, Université de Bordeaux, Medizinische Universitat Graz).[66] In each patient-specific model, 30 pacing sites were distributed uniformly throughout the atria using a point repulsion algorithm. A decremental pacing protocol consisting of 14 pulses with cycle lengths decreasing from 300 to 150 ms in 25 ms intervals was delivered at each site to induce LAFL. LAFL was categorized as inducible in a given atrial model if self-sustained reentrant activity persisted throughout the duration of the simulation after the last pacing stimulus was delivered.

Identification and Ablation of Minimum Cuts in Reentrant Wave Propagation

Figure 6:
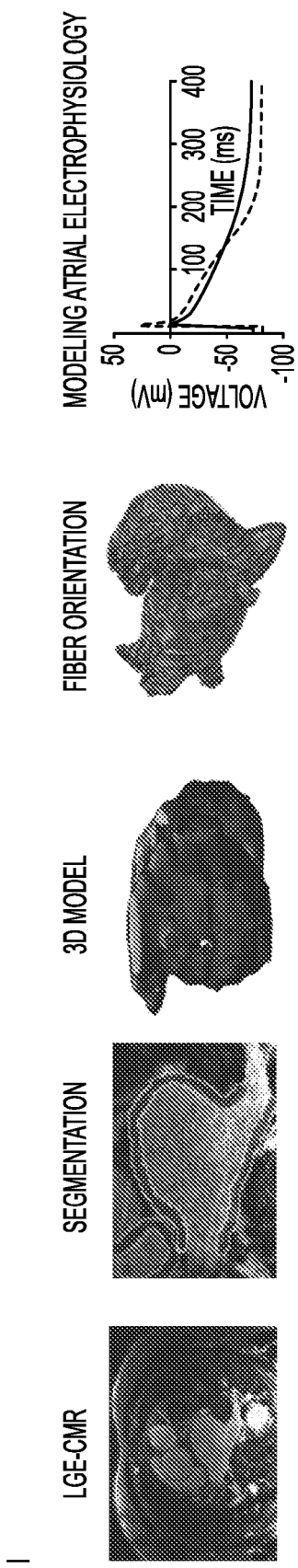
FIG. 6 depicts model generation and identification of minimum cuts in reentrant flow propagation. I: Pipeline to construct MRI-based models of fibrotic human atria. (A): Representative LGE-CMR slice of human atria. (B): Atrial tissue segmentation into fibrotic (green) and non-fibrotic (gray) regions. (C): 3D reconstruction of atrial geometry. (D): Fiber orientation in atrial model. (E): Atrial action potentials in fibrotic (green) and non-fibrotic tissue (gray). II: Schematic for identifying minimum cuts in reentrant flow propagation, represented as a flow network. The minimum cut of the flow network is indicated with a dashed line.
Figure 6:
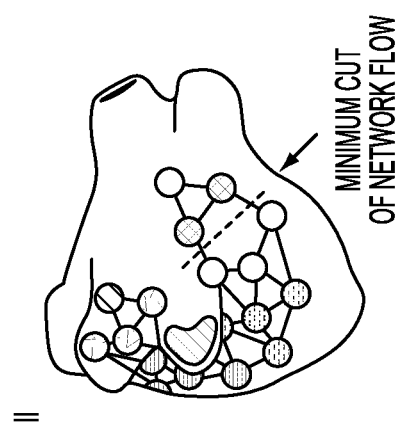

We developed a novel methodology to automatically identify, based on the simulated reentrant circuits, the optimal ablation target for each LAFL morphology. We represented wave propagation during one cycle of reentry as a flow network. A flow network is a mathematical graph that models directional movement between interconnected objects. Interconnected objects are represented as vertices in a graph; links between adjacent pairs of vertices, where flow can pass through, are called edges; and the maximum possible flow between two adjacent vertices is termed edge capacity. The minimum cut (MC) in a flow network represents the number of edges that, when removed, separate the network into two disconnected components (FIG. 6, II).

In this study, each vertex in the flow network corresponded to an element in the patient-derived mesh. Two vertices in the network were defined to be adjacent to each other if they 1) corresponded to elements that shared a common face and 2) if the difference in activation time between these elements was less than 20 ms. An edge in the flow network corresponded to the shared face between adjacent vertices. The capacity of a network edge was defined to be equal to the cross sectional area of the corresponding face. The MC was the minimum set of faces between finite elements in the mesh that partitioned the flow network into two disconnected components and was determined using the Boykov-Kolmogorov algorithm.[67] The MCs are the in silico equivalent of the minimum set of ablation lesions needed to terminate LAFL. In silico ablation was performed by rendering all atrial tissue within 2 mm of the MC non-excitable.

Advantages of the Minimum Cut Approach to Identify Ablation Targets

Figures 7A, 7B:
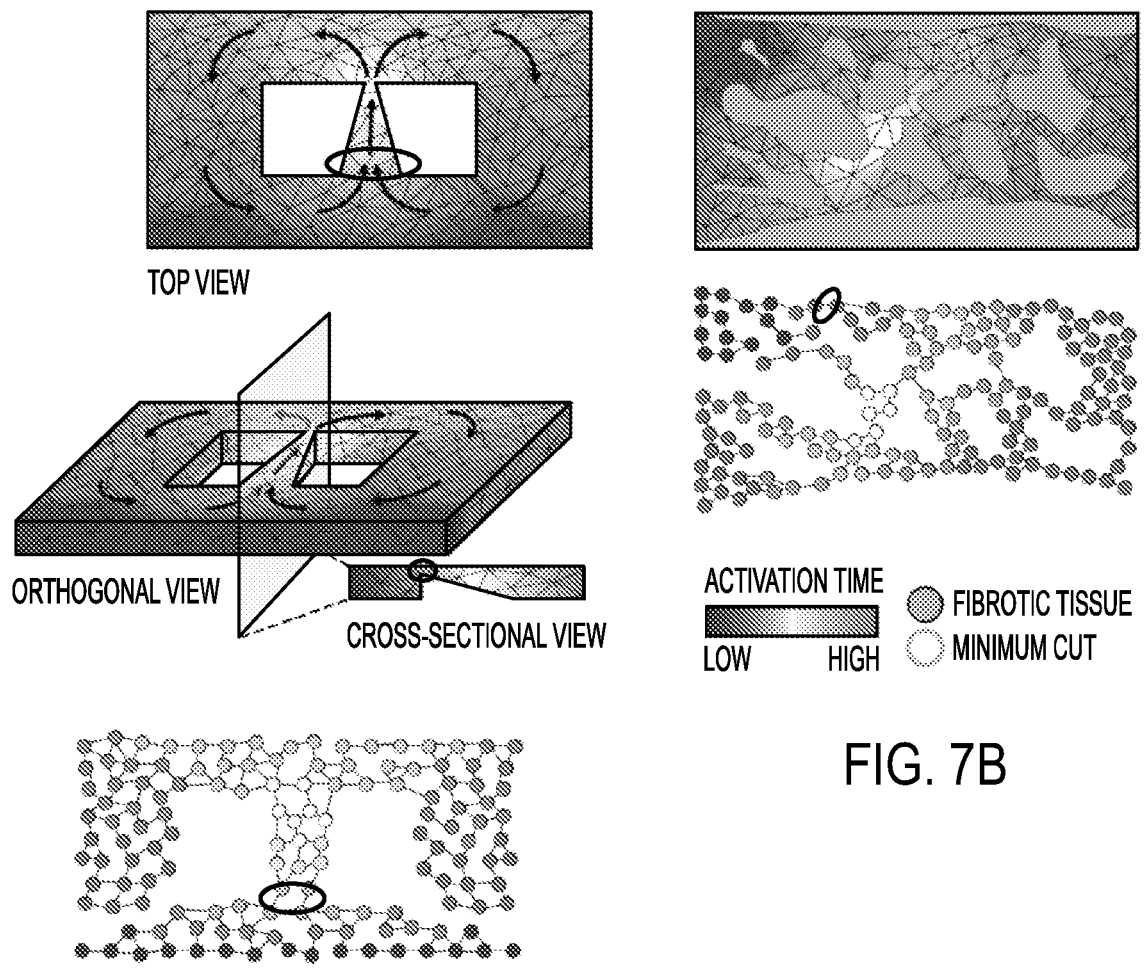
FIGS. 7A-7B depict schematics for identifying minimum cut in cases of non-obvious reentry. Activation maps showing reentry in tissue with varying wall thickness (A) and heterogeneous distribution of fibrotic tissue (B). The corresponding flow network is indicated below the activation maps and the location of the minimum cut is highlighted in cyan.

Two examples illustrating the advantages of the minimum cut (MC) approach to identify ablation targets are presented in FIGS. 7A and 7B. FIG. 7A shows a figure-of-eight reentry, in which the critical isthmus of the reentrant circuit occurs over a region with varying wall thickness. A 2D activation map on the top surface suggests that the exit site of the reentrant circuit on that surface should be ablated. However, flow network analysis of the full 3D reentrant circuit indicates that the optimal ablation target is at a different location—the MC is located at the entry site of the reentrant circuit, where tissue is thin and thus a minimum amount of tissue will be ablated to terminate the reentry. FIG. 7B highlights another example, where a reentrant wave propagates around a heterogeneously distributed fibrotic tissue. In this case, determining the ablation target(s) based on a visual inspection of the activation map is difficult. Using network flows analysis to identify the MC provides an objective, automated method to find the smallest amount of tissue needed to interrupt reentrant wave propagation.

Comparison of in Silico and Clinical LAFL and Ablation Targets

Each patient in this study underwent a clinical electrophysiology study (EPS) to treat LAFL. For each patient, the critical isthmus location of the reentrant circuit in LAFL found by entrainment mapping was compared to the one found in LAFL simulations. Additionally, in each patient, the lengths and locations of ablation lesions that terminated LAFL were compared to the MCs that were ablated in the patient-specific models. This comparison was retrospective, but conducted in a double-blinded fashion—researchers who conducted simulations were blinded to procedures and clinicians who performed procedures were blinded to simulations. Detailed information about clinical EPS is in supporting material.

Results

Patient Characteristics

Figure 8:
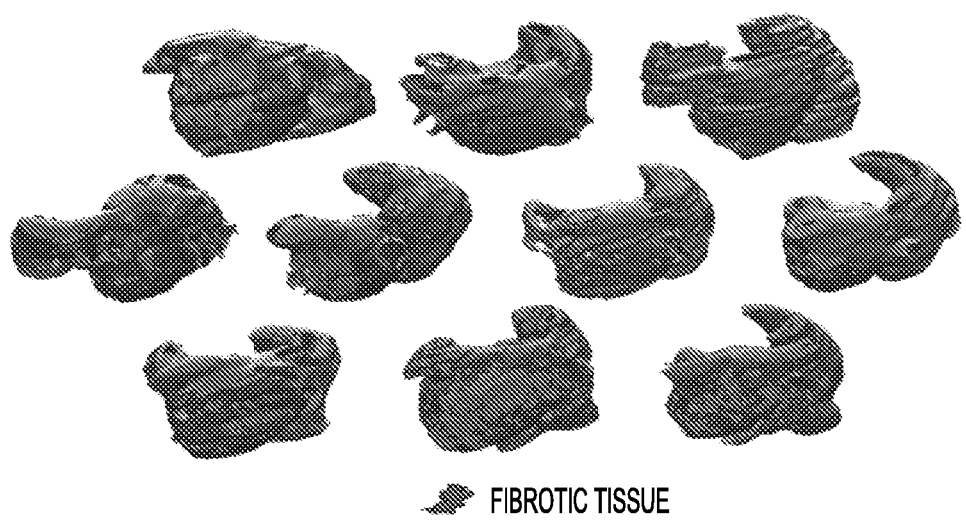
FIG. 8 depicts 3D patient-specific atrial models. Personalized 3D models of all ten patient atria reconstructed from LGE-CMR scans.

The baseline characteristics for all 10 patients are presented in Table 1. The mean patient age was 67±13 years (3 female, 7 male); the mean left atrial volume in each patient was 42.9±10.3 mL; and every patient had a previous pulmonary vein (PV) isolation procedure to treat AF. The reconstructed atrial models with individualized representations of fibrosis derived from LGE-CMR for all 10 patients are shown in FIG. 8. The mean proportion of fibrotic tissue in the atria was 24.5±12.89%, and most of the fibrotic tissue (56.61±29.37%) was located in the posterior left atrium (PLA).

TABLE 1

Baseline Patient Characteristics

| Patient | Age | Sex | Prior Procedures | Heart Disease | Diabetes | Hypertension | LA Volume (mL/mm$^2$) | Fibrosis Extent (%) |
|---|---|---|---|---|---|---|---|---|
| 1 | 55 | F | PVI | None | No | Yes | 32.8 | 44.27 |
| 2 | 74 | M | PVI | None | No | No | 45.38 | 14.67 |
| 3 | 37 | F | PVI | None | No | No | 54.05 | 30 |
| 4 | 63 | M | PVI | None | No | No | 52.42 | 27.98 |
| 5 | 75 | M | PVI, CABG, MAZE | None | No | No | 34.226 | 44.74 |
| 6 | 74 | M | PVI | None | No | No | 49.63 | 18.28 |
| 7 | 78 | M | PVI | None | No | No | 59.01 | 29.8 |
| 8 | 79 | F | PVI | None | Yes | No | 34.47 | 14.5 |
| 9 | 67 | M | PVI, CABG, MAZE | None | No | No | 33.55 | 13.2 |
| 10 | 70 | M | PVI | None | Yes | Yes | 33.52 | 8.27 |

PVI = pulmonary vein isolation;
CABG = coronary artery bypass graft;
MAZE = Cox-Maze procedure

TABLE 2

Comparison of simulation and clinic cycle lengths

| PATIENT | SIMULATION (ms) | CLINIC (ms) |
|---|---|---|
| 1 | 240 | 300 |
| 2 | 290 | 280 |
| 3 | 300 | 300 |
| 4 | 240 | 280 |
| 5 | 255 | 290 |
| 6 | 360 | 300 |
| 7 | 350 | 350 |

Figures 9A, 9B:
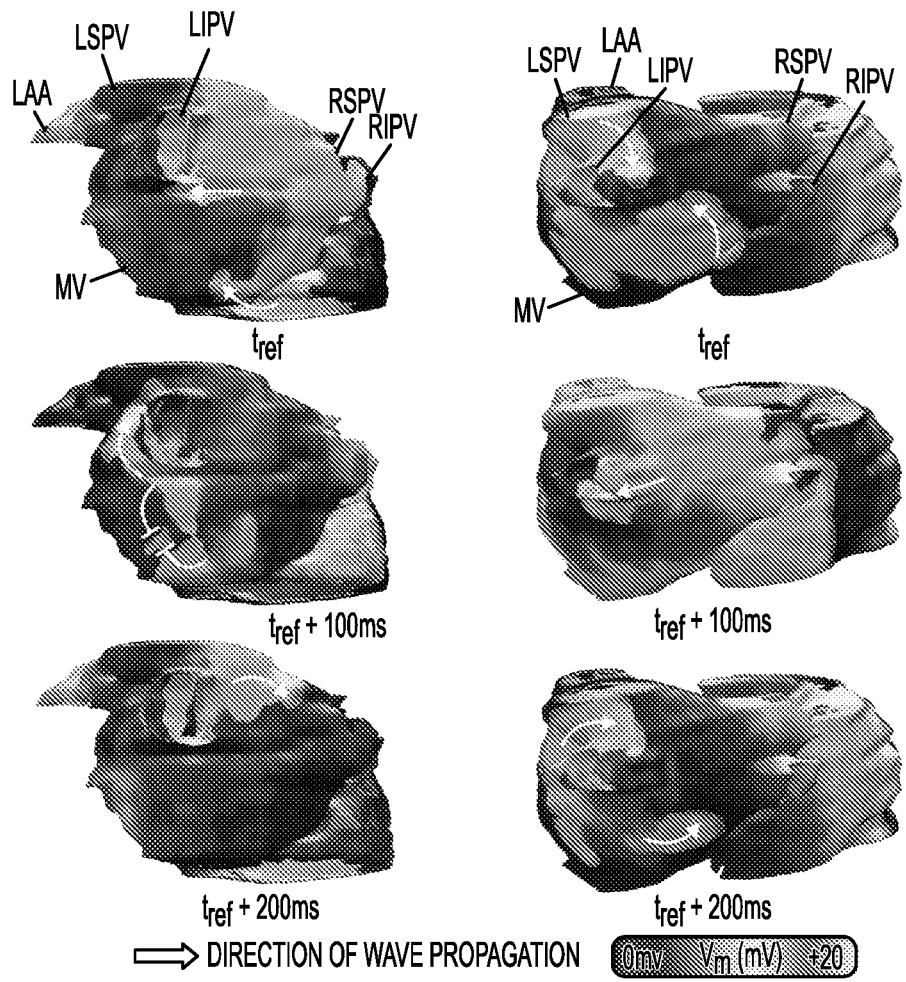
FIGS. 9A-9B depict examples of LAFL sustained by peripulmonary vein reentry. Transmembrane maps showing reentry around the left inferior pulmonary vein in model #1 (A) and figure-of-eight reentry in model #2 (B). The counterclockwise circuit in the figure-of-eight reentry is around the left inferior pulmonary vein and the clockwise circuit is in the posterior left atrium.
Figure 10:
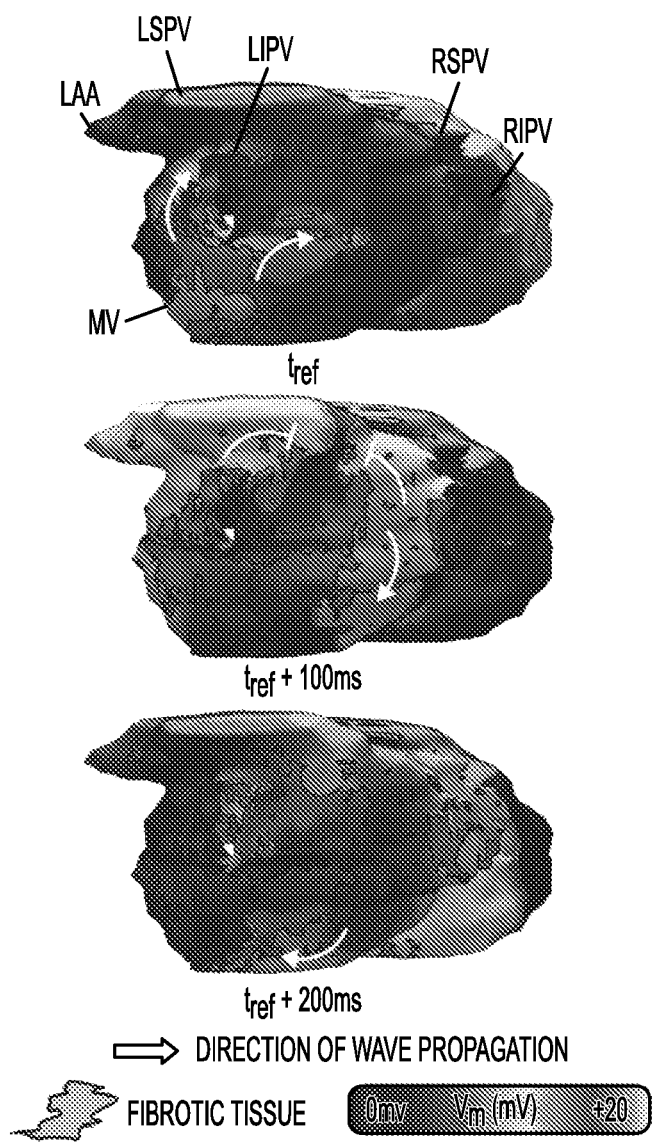
FIG. 10 depicts examples of LAFL sustained by perimitral reentry. Transmembrane voltage maps showing figure-of-eight reentry in model #3 (A) and model #4 (B). In both cases, the clockwise circuit in the figure-of-eight reentry is around the mitral valve and the counterclockwise circuit is in the posterior left atrium.
Figures 11A, 11B:
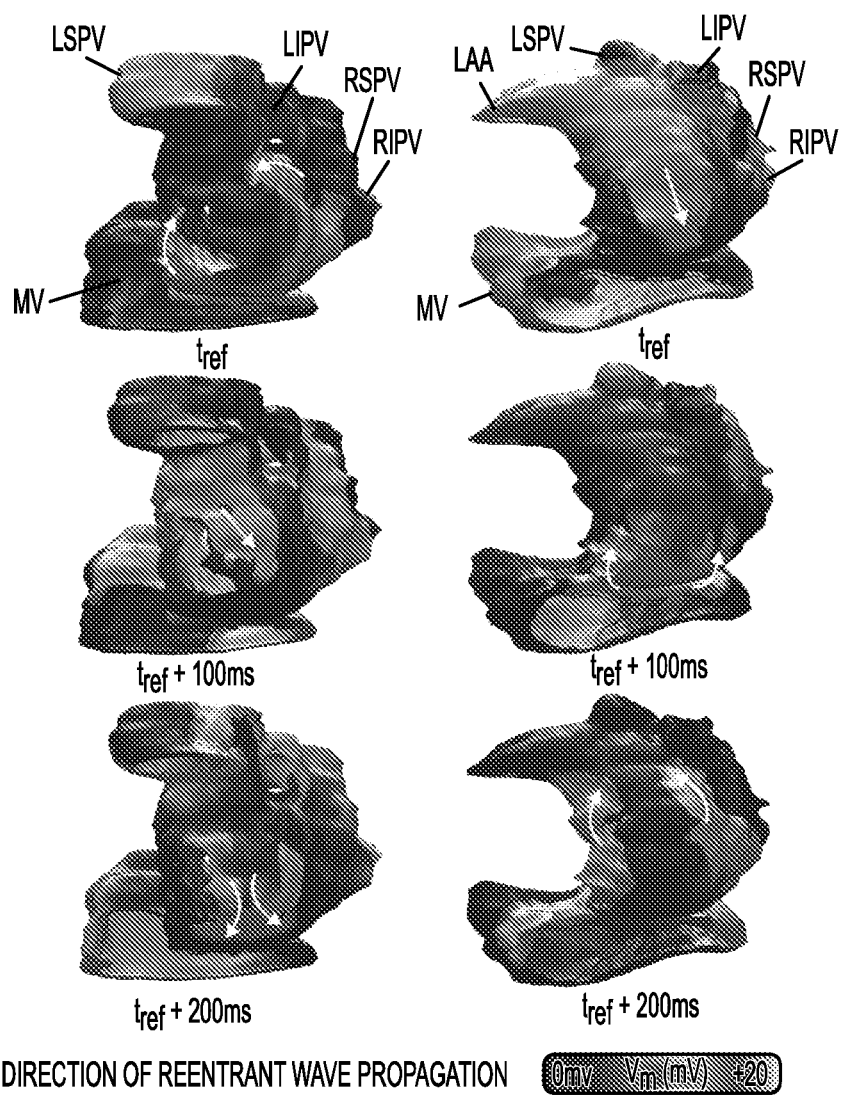
FIGS. 11A-11B depict examples of LAFL sustained by reentry around fibrotic tissue in posterior left atrium. Transmembrane voltage maps showing reentry around fibrotic tissue in the posterior left atrium for model #5. Fibrotic tissue is highlighted in green.

PVI = pulmonary vein isolation;
LIPV = left inferior pulmonary vein;
PLA = posterior left atrium In Silico LAFL Reentry Morphologies In silico LAFL was successfully induced in 7 out of 10 models. In these 7 models, a single stable macro-reentrant circuit was induced, which was unique to the model. Compared to the models not inducible for arrhythmia, the 7 LAFL-inducible models contained a significantly greater proportion of fibrotic tissue (30.0±11.5% vs 12.0±3.3%, p<0.05). In the LAFL-inducible models, there were three types of persistent reentry morphologies: peripulmonary vein reentry, perimitral reentry, and reentry around fibrotic tissue in the PLA. FIGS. 9A and 9B show transmembrane voltage (Vm) maps of peripulmonary vein reentry at three instants of time in models #1 and #2. In model #1, a single wave rotating clockwise around the left inferior PV sustained LAFL (FIG. 9A). A figure-of-eight reentry perpetuated LAFL in model #2 (FIG. 9B), where one clockwise reentrant wavefront propagated around the left inferior pulmonary vein (LIPV) and the other adjacent counterclockwise reentrant wavefront propagated in the PLA. Examples of perimitral reentry in models #3 and #4 are shown in FIG. 10. In both models, a figure-of-eight reentry, with one clockwise reentrant wavefront around the mitral valve and an adjacent counterclockwise reentrant wavefront in the PLA, sustained LAFL. FIG. 11 depicts a clockwise reentry that propagates around fibrotic tissue in the PLA, sustaining LAFL in model #5. The reentry morphologies of two additional patients are presented in Supplementary Materials and FIG. 12 and FIG. 13. Table 2 presents a summary of the clinical and in-silico cycle lengths for the 7 in-silico inducible patients.

Ablation of Minimum Cut

In each model inducible for LAFL, the MC corresponding to the specific reentry morphology was determined and ablation delivered as described in Methods. The MC was unique to each model. FIG. 14A-C illustrate the MCs (cyan) in models #2, #3, and #4, respectively, overlaid on LAFL activation map. In silico ablation at the MC terminated LAFL in these three models, as demonstrated in FIG. 14D-F.

FIG. 15A-B show the MCs in models #1 and #5. In silico ablation of these MCs uncovered additional LAFLs with different reentry morphologies. In the original LAFL morphology in model #1, a counterclockwise wavefront split from the reentrant wave near the LIPV and extinguished upon collision with a clockwise wavefront that emanated from the reentrant wave in the posterior inferior left atrium (FIG. 9A). Ablation of the MC prevented the emergence of the counterclockwise wavefront, so the clockwise wavefront subsequently propagated along excitable tissue inferior to the LIPV and caused the formation of a sustained, figure-of-eight reentry in the PLA with a cycle length of 460 ms (FIG. 15C).

In the original LAFL morphology in model #5, a counterclockwise wavefront split from the reentrant wave near the right inferior PV. This wave collided with a clockwise wavefront that broke off from the reentrant wave at an earlier time point near the LIPV. The resulting collision caused both wavefronts to terminate (FIG. 11). Ablation of the MC prevented the formation of the counterclockwise wavefront, so the clockwise wavefront led to a sustained reentrant circuit with a cycle length of 475 ms around the LIPV FIGS. 15-18.

The MCs in the emergent post-ablation reentry morphologies are shown in FIGS. 15A and 15B for models #1 and #5 respectively. Ablation of these MCs terminated the arrhythmia in both cases (FIGS. 16C and 16D). Information detailing MC locations and ablation outcomes in the remaining models, #6 and #7, is provided in FIG. 18.

Comparison Between in Silico and Clinical LAFL Critical Isthmus Locations

Table 3 details the comparison between LAFL critical isthmus locations found in patient-specific models and clinical EPS. Entrainment mapping in clinical EPS and in silico simulations identified the critical isthmus of LAFL reentrant circuits to be located in the same regions of the atria in patients 1 (LIPV ostium), 3 (mitral isthmus), 4 (PLA), 5 (PLA), 6 (mitral isthmus), and 7 (mitral isthmus). In patient 2, simulations identified the critical isthmus of the LAFL reentrant circuit to be located near the ostium of the LIPV. In clinical EPS for this patient, multiple reentrant circuits with different activation sequences were observed and LAFL was not successfully entrained. However, LAFL terminated upon application of ablation lines connecting right and left PV isolation lesions, thus suggesting the region between the right and left PVs was involved in the reentrant circuit.

TABLE 3

Comparison of critical isthmus locations of LAFL reentrant circuits in simulation and clinic

| PATIENT | SIMULATION | CLINIC |
|---|---|---|
| 1 | LIPV Ostium | LIPV Ostium |
| 2 | LIPV Ostium | Not Mapped |
| 3 | Mitral Isthmus | Mitral Isthmus |
| 4 | PLA | PLA |
| 5 | PLA | PLA |
| 6 | Mitral Isthmus | Mitral Isthmus |
| 7 | Mitral Isthmus | Mitral Isthmus |

PVI = pulmonary vein isolation;
LIPV = left inferior pulmonary vein;
PLA = posterior left atrium Comparison Between in Silico and Clinical Ablation Targets FIG. 20 depicts a comparison between simulation findings and clinical findings. As can be seen for these three examples, simulations were performed in personalized models and compared to clinical findings in the corresponding patients. For patient 1, reentrant circuit was observed between inferior PVs, Tachycardia cycle length was 350 ms, and ablation at sites are shown in figure terminated the left atrial flutter. For patient 2, reentrant circuit was observed near the mitral valve, tachycardia cycle length was 300 ms, and ablation at sites shown in figure terminated the left atrial flutter. For patient 3, microentrant flutter was observed in PLA. Tachycardia cycle length was not determined and ablation at the sites of microreentrant flutter led to faster flutter which degenerated into atrial fibrillation.

Summary Table 4, FIG. 17 (models 1-5), and FIG. 18 (models 6 and 7) present comparisons of the lengths and locations of the ablation targets that terminated LAFL in simulations and in clinical EPS for all patients. The ablation targets in simulation were the MCs in the flow network of reentrant wave propagation in in silico LAFL and the ablation targets in clinical EPS were determined from entrainment mapping during the procedure. Simulation ablation targets were similar in location but smaller in length than clinical ablation targets (2.8±1.5 cm in simulation vs 4.8±1.7 cm in EPS, p<0.05).

TABLE 4

Comparison of lengths and locations of simulation and clinical ablation targets

| | SIMULATION | | CLINICAL | |
|---|---|---|---|---|
| PATIENT | Size | Strategy | Size | Strategy |
| 1 | Two Lines, 1.4 cm and 1.82 cm | LIPV to Fibrosis in PLA | Set of Lesions, 2.75 × 0.93 cm | Inferolateral from LIPV |
| 2 | Two Lines, 0.96 cm and 1.56 cm | LIPV to Fibrosis in PLA | One Line, 3.32 cm | Left PVI to Right PVI |
| 3 | One Line, 3.22 cm | MV to Fibrosis in PLA | Set of Lesions, 3.84 × 1.06 cm | MV to LIPV |
| 4 | One Line, 2.63 cm | MV to Fibrosis in PLA | One Line, 2.98 cm | MV to Right PVI |
| 5 | One Line, 2.85 cm | MV to Fibrosis in PLA | One Line, 2.85 cm | MV to PLA |
| 6 | One Line, 3.85 cm | MV to Fibrosis in PLA | One Line, 4.78 cm | MV to Fibrosis in PLA |
| 7 | Two Lines, 3.78 cm and 6.22 cm | LSPV to MV and LSPV to RIPV | Three Lines, 3.54 cm, 6.31 cm, and 6.12 cm | LIPV to MV, LSPV to RSPV, and LIPV to RIPV |

Figure 12A:
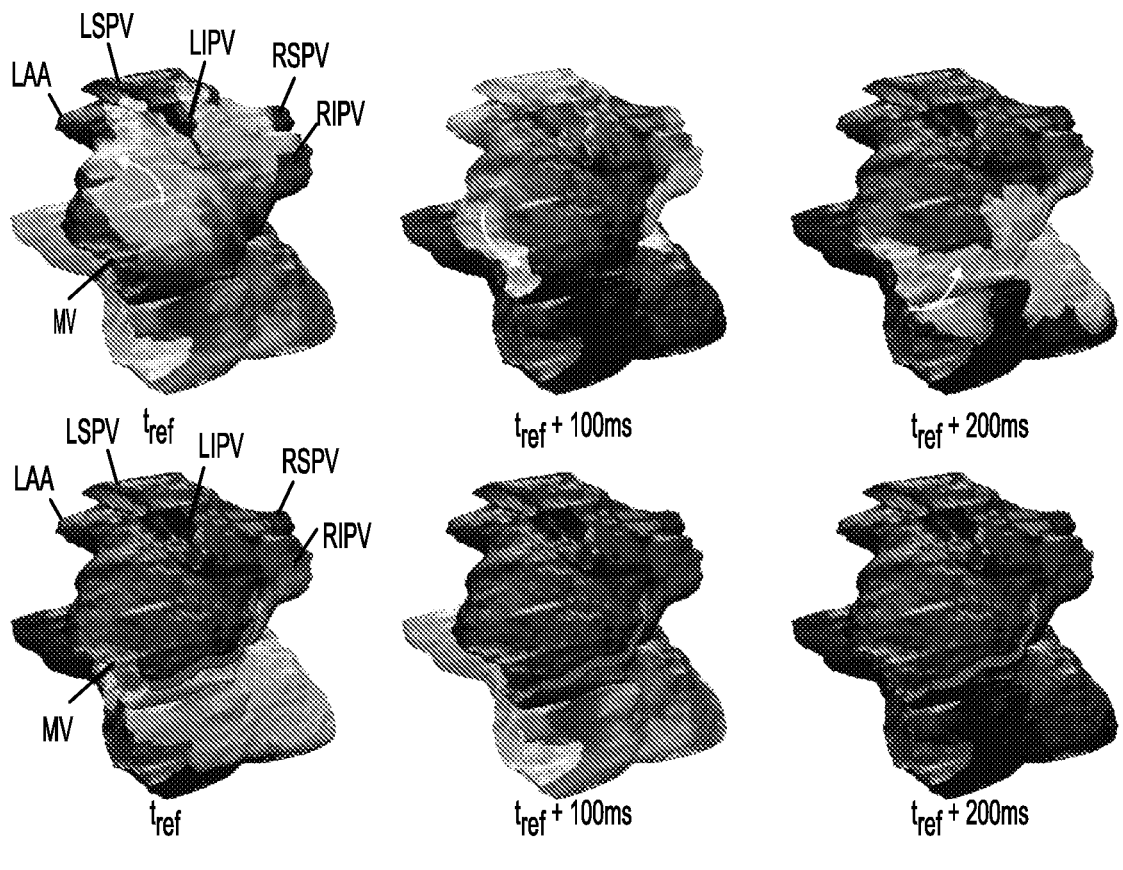
FIG. 12 depicts reentry, minimum cut, and ablation in model #6. (A) Transmembrane maps showing reentry around the mitral valve. Transmembrane maps showing LAFL termination after in silico ablation was applied (red). (B) Location of minimum cut (cyan) of reentrant flow propagation overlaid on activation map of LAFL episode.

PVI = pulmonary vein isolation;
LIPV = left inferior pulmonary vein;
PLA = posterior left atrium;
MV = mitral valve;
LSPV = left superior pulmonary vein;
RSPV = right superior pulmonary vein In model #1, the simulation ablation targets included two segments of atrial tissue (1.40 cm and 1.82 cm in length), which both extended from the LIPV to fibrotic tissue in the PLA (FIG. 12Ai). In clinical EPS for this patient, a region of tissue (lesion dimensions: 2.75 cm×0.93 cm) inferior to the LIPV was ablated to terminate LAFL FIG. 17Aii).

The in silico ablation targets in model #2 were two segments, (0.96 cm and 1.56 cm in length) which both extended from the LIPV to fibrotic tissue in the PLA. In clinical EPS, an ablation line (3.32 cm-long) that connected right and left PV isolation lesions terminated the arrhythmia (FIG. 17Bii).

In model #3, the simulation ablation target was a segment of atrial tissue (3.22 cm in length) that connected the mitral valve to fibrotic tissue inferior to the LIPV (FIG. 17 Ci). A region of tissue joining the mitral valve to the LIPV (lesions dimensions: 3.84 cm×1.06 cm) was ablated in clinical EPS to terminate LAFL (FIG. 17Cii).

The simulation ablation target in model #4 was a segment (2.63 cm in length) of atrial tissue from the mitral valve to fibrotic tissue inferolateral from the RIPV (FIG. 17 Di). In EPS, an ablation line (2.98 cm in length) from the mitral valve to the right PV isolation lesions was executed to terminate LAFL. This ablation line converted the arrhythmia to AF (FIG. 17Dii) and cardioversion was applied to terminate AF. After cardioversion, LAFL was non-inducible after application of further programmed electrical stimulation.

Finally, in model #5, the simulation ablation target was a segment of atrial tissue (2.98 cm in length) connecting the mitral valve to fibrotic tissue in the PLA (FIG. 17 Ei). In EPS, ablation lesions (2.85 cm) extending from the mitral valve to atrial tissue in the PLA terminated LAFL (FIG. 17Eii).

Reentry Morphologies, Minimum Cut Locations, and Ablation in Models #6 and #7

Figure 12B:
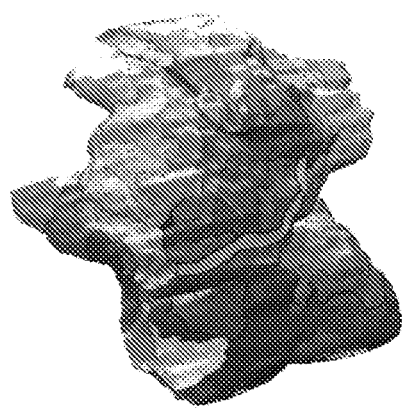

LAFL was sustained by a counter perimitral reentry in model #6 (FIG. 12A) and by a clockwise perimitral reentry in model #7 (FIG. 13A). FIG. 12 and FIG. 13 illustrate the MCs (cyan) in models #6 and #7 overlaid on the activation maps of the LAFL episodes. In model #6, in silico ablation at the MC terminated LAFL (FIG. 13C). In model #7, in silico ablation at the MC interrupted the perimitral reentry and uncovered a peripulmonary vein reentry around the right inferior PV (FIG. 12C). The MC of the emergent LAFL episode was located along atrial tissue that extended from the left superior PV to the right inferior PV (FIG. 12D), and in silico ablation of this region terminated the arrhythmia (FIG. 12E).

Comparison Between in Silico and Clinical Ablation Targets in Models #6 and #7

In model #6, the simulation ablation target was a segment of tissue (3.85 cm) connecting the mitral valve to fibrotic tissue in the posterior left atrium (FIG. 18 Bi). In EPS, a similar set of ablation lesions (4.78 cm) joining the mitral valve to tissue in the posterior left atrium terminated LAFL (FIG. 18 Bii).

In model #7, the simulation ablation targets included two segments of atrial tissue, one extending from the mitral valve to the left superior PV (3.78 cm) to terminate perimitral reentry and another extending from the left superior PV to the right inferior PV (6.22 cm) to terminate the post-ablation peripulmonary vein reentry (FIG. 18 Ai). In clinical EPS for this patient, ablation was applied in the region between the mitral valve and the left inferior PV (3.54 cm) to terminate perimitral reentry (FIG. 18 Aii). After ablation, LAFL morphology changed and additional lesions were placed to connect right and left PV isolation lesions (two lines of length 6.31 and 6.12 cm). The arrhythmia was terminated using cardioversion and was non-inducible after application of further programmed electrical stimulation. Additional ablation lesions were placed in that patient to electrically isolate the PVs from the left atria.

FIG. 19 depicts LGE-MRI data from 7 LAFL patients was used to construct atrial models incorporating scar tissue (FIG. A). In-silico rapid pacing induced LAFL in all patient models.

Previously validated software was used to identify ablation targets and perform ablation in the models. Following registration to MRI images, in silico ablation sites were compared to lesions delivered during intracardiac electrophysiology study.

LAFL with a macro-reentrant propagation pattern was induced in all models. Example is in FIG. 19B; the model RC is consistent with the clinical RC, which necessitated ablation lines connecting the PV isolation loops to treat LAFL (FIG. 19C). In silico ablation targets, typically identified by software as tissue connecting fibrotic patches (FIG. 19B) rendered the atria non-inducible for LAFL. Connection of the PVI loops slightly inferior to the simulated RC had a similar effect clinically.

The feasibility of using personalized atrial models was tested to identify ablation targets for LAFL. To achieve this goal, we simulated LAFL in 10 patient-specific models with individualized atrial geometry and fibrotic tissue distribution derived from clinical LGE-CMR scans. We developed a novel graph-cutting algorithm to identify the MC in the flow network representing reentrant wave propagation, and we demonstrated that targeting MCs for ablation in each atrial model successfully terminated LAFL. The in silico ablation targets were compared to those executed in the clinic to terminate LAFL in patients. The main contributions of our study can be summarized as follows:

1. We present the first proof-of-concept study demonstrating that patient-specific models can be used to accurately simulate LAFL and predict the optimal ablation targets;

2. Graph theory tools identified the optimal ablation targets (the MC in reentrant wave propagation);

3. Ablation of MCs terminated LAFL or uncovered additional LAFL morphologies with slower tachycardia cycle lengths; and, 4. Ablated MCs that terminated LAFL in simulation were smaller in length and similar in location to the ablation lesions that, additional to PV isolation lines, terminated LAFL in EPS.

Characteristics of in Silico LAFL

The LAFLs observed in our image-based simulations included sustained reentry involving the mitral valve, LIPV, or large regions of fibrotic tissue in the PLA. These reentry morphologies are consistent with LAFLs observed in clinical studies.[81, 91] For instance, Jaïs et al.[81] showed that in 22 patients with LAFL, 7 patients had reentry around the mitral valve, 1 had reentry around the left PVs, and 4 had reentry around electrically silent areas in the PLA.

Similarly, Ouyang et al.[91] showed that in 28 patients with LAFL, 9 had reentry around the mitral valve, 13 had reentry around the left PVs, and 3 had reentry around electrically silent areas in the PLA. The electrically silent areas, defined in electroanatomical mapping as atrial tissue where electrical potential recordings are indistinguishable from noise, can be viewed as analogous to regions with dense fibrosis in our models, which exhibit significantly inhibited conduction due to decreases in tissue conductivities and in the upstroke velocity in myocyte action potentials. Experimental studies in both animals and isolated human tissue have shown that electrically silent areas occur in dense fibrotic tissue regions.[92]

Furthermore, the critical isthmus locations of LAFL reentrant circuits found in simulations and clinical EPS matched in 6 out of 7 patients. In the unsuccessful case, LAFL could not be entrained during clinical EPS. This finding of successful correspondence between simulation and clinical EPS in a few patients suggests that it may be possible for patient-specific models to non-invasively locate reentrant circuits in LAFL, which will benefit pre-procedural treatment planning for this arrhythmia. However, a larger prospective clinical study comparing activation maps of LAFL found in simulation and EPS is still needed to validate the application of patient-specific models for LAFL management.

Identification of Ablation Targets Using Network Flows Analysis

In order to terminate LAFLs in simulation, we developed an algorithm based on network flow analysis to identify the minimum amount of tissue needed to interrupt electrical wave propagation during reentry.[90]

Network flows analysis has been routinely applied in many other non-medical fields, such as image segmentation, railway transportation, and telecommunications.[93]

In this paper, we present the first application of network flows analysis in cardiac electrophysiology to identify optimal ablation targets (the MCs). A major advantage of the new approach is that finding the optimal ablation targets in each model was done automatically, without manual intervention. The development of an automatic predictor of optimal ablation targets is an important advancement towards the use of patient-specific atrial models to non-invasively guide clinical ablation. Additionally, the MC approach identified the optimal ablation targets based on information about the 3D reentrant circuits in each 3D fibrotic substrate.

The MC in each LAFL was located in short segments (lengths ranging from 1.40 to 3.85 cm) of atrial tissue involved in the reentrant circuit that connected nonconductive anatomical barriers such as the mitral valve or LIPV to fibrotic tissue regions. Ablation of the MC prevented the reentrant wave from circumnavigating the ablation lesion and propagating along the original reentrant circuit pathway. This strategy is analogous to strategies espoused in clinical studies of interatrial reentrant tachycardia after congenital heart surgery,[94] which show that extending ablation lesions from fibrotic scar caused by surgical incisions to natural atrial boundaries like the inferior vena cava, superior vena cava, or the tricuspid annulus is more effective in terminating arrhythmia than executing focal ablation lesions in the critical isthmus of the reentrant circuit.

Post-Ablation LAFL

Ablation of the MC successfully interrupted wave propagation in the original reentrant circuit that produced LAFL in all seven models. This led to LAFL termination in four of the models and in the emergence of new LAFL morphologies in the remaining three cases. In the original LAFL for the latter three cases, two wavefronts (one clockwise and one counterclockwise) split from the reentrant circuit at different time points and collided with each other. This collision extinguished both wavefronts, but did not affect wave propagation of the reentrant circuit that sustained LAFL. Ablation of the MC eliminated the formation of the counterclockwise wavefronts in both models, so the clockwise wavefront propagated along excitable tissue to cause the formation of a new and slower LAFL.

These findings demonstrate the importance of understanding and appreciating the specific pathway of wave propagation in the entire atria during LAFL as opposed to just identifying the reentrant circuit critical isthmus, since ablation can uncover additional reentrant morphologies. The transformation of reentry morphologies that sustain LAFL by catheter ablation has also been noted in clinical studies. For example, Ouyang et al.[91] described a transformation of LAFL, reporting an absence of electrical activity in the ablated region determined to be the critical isthmus of the reentrant circuit; remapping the transformed tachycardia revealed that another region of the atria, which was a bystander in the original reentry, was now the critical isthmus of the new reentry circuit. Similarly, Rostock et al.[95] noted the transformation of reentry morphologies in atrial tachycardia after ablation in 45 patients and reported that the mean cycle length of the postablation tachycardia was longer than the cycle length of the original tachycardia (320±88 ms vs 274±40 ms).

Comparison of Simulation and EPS Ablation Lesions

Finally, we compared the ablated MCs in simulations to ablation targets that successfully terminated LAFL in EPS. In the 7 LAFL-inducible models, the ablation lines were shorter (2.8±1.5 cm in simulation vs 4.8±1.7 cm in EPS) but in locations fairly similar to the ablation lesions, outside of PV isolation lines, that terminated LAFL in EPS. The strategies of determining ablation lesions in EPS varied from patient to patient, but generally involved connecting non-conductive barriers to each other (i.e., connected mitral valve to LIPV in patient #3 and the right and left PV isolation lesions in patient #2). This is similar to the ablation strategy via MCs in simulations, where non-conductive anatomical barriers were connected to regions of fibrotic tissue with reduced capacity for excitation and conduction. Previous image-based simulation studies from our team have also demonstrated a successful correspondence between in silico and EPS ablation targets for ventricular tachycardia.[97]

These studies highlight the potential of patient-specific models to noninvasively determine the optimal ablation targets for complex cardiac arrhythmias due to a reentrant mechanism. The present study is a retrospective proof-of-concept, and prospective studies are required to further support the approach.

Study Limitations

In three of the models, LAFL was not inducible in simulations, despite the presence of arrhythmia in clinical EPS. This may be due to the low amount of fibrotic tissue in these patients identified by LGE-CMR. In this study, voxels with an IIR above 0.97 in LGE-CMR were segmented to correspond to fibrotic tissue.[82]

This threshold overcomes the limitation that LGE-CMR voxel intensities vary between patient scans due to differences in surface coil proximity, contrast dose, and body mass index.[98]

However, the identification of a threshold in LGE-CMR to represent fibrotic tissue is still controversial and it is unknown if the threshold chosen in our study leads to the best correlation between simulation and clinical reentry morphologies.

Another limitation of this study was that activation mapping was not performed in these patients, since ablation targets were primarily determined from entrainment mapping during clinical EPS. Therefore, we could not compare the exact reentry patterns in LAFL found in simulation to LAFL observed in clinic. A future prospective study with detailed comparisons of dense activation maps, combined with entrainment mapping at putative circuit sites and larger study population size is needed to validate image-based simulation for LAFL treatment planning.

Finally, functional changes in electrophysiology might be contributing to LAFL in patients, which our models, designed to represent the contribution of the structurally-remodeled substrate only, cannot capture.

This work was supported by the National Institutes of Health [DP1-HL123271 to N.A.T., R01-HL116280 to S.N.]; National Science Foundation [CDI 1124804 to N.A.T., Graduate Research Fellowship to S.Z., K23-HL089333 to S.N.]; ARCS Foundation [to S.Z.], a Biosense-Webster grant [to S.N.], the Roz and Marvin H Weiner and Family Foundation, the Dr. Francis P. Chiaramonte Foundation, the Marilyn and Christian Poindexter Arrhythmia Research Fund, and the Norbert and Louise Grunwald Arrhythmia Research Fund.

Thus, some embodiments of the current invention differ from PCT/US2014/068215 based on an application to a different atrial arrhythmia—flutter. We also find the ablation targets differently from PCT/US2014/068215. We can first find the critical isthmus of the reentrant wave or the zone of slow conduction, or the minimum cut region. We can ablate that region. We can then ablate a line connecting this lesion with the nearest non-conductive anatomical barrier, such as the mitral valve. If the pulmonary vein is the nearest non-conductive barrier, we can first conduct pulmonary vein isolation (encircling) lesion.

In one embodiment, the patient cannot be ablated only with a starting point lesion which is based on finding area of slow conduction of critical isthmus of rotation. This is just initial lesion and then the lesion are extended and connected to non-conductive regions.

Thus, embodiments of the present invention can include the following steps:
1. Transecting the critical isthmus with linear ablation lesion
2. Identifying connecting targets (i.e., points where the transection lesion endpoints must extend so that a wave cannot propagate around the lesion)
3. If connecting target is near a PV, executing or completing PV isolation ablation lesions
4. Executing linear lesions to extend the transection lesion endpoints to connecting targets In some embodiments of the present invention, the method includes identifying an optimal ablation location to render the individual non-inducible for LAFL. Further, in some embodiments, the ablation of the one or more ablation lesion locations and the ablation of at least one line connects the ablation lesions with the nearest non-conductive anatomical barrier. Embodiments can also include minimum cut techniques, as discussed herein.

REFERENCES

1. Feinberg W M, Blackshear J L, Laupacis A, Kronmal R, Hart R G. Prevalence, age distribution, and gender of patients with atrial fibrillation. Analysis and implications. Arch Intern Med. 1995; 155:469-473
2. Miyasaka Y, Barnes M E, Gersh B J, Cha S S, Bailey K R, Abhayaratna W P, Seward J B, Tsang T S. Secular trends in incidence of atrial fibrillation in Olmsted county, Minn., 1980 to 2000, and implications on the projections for future prevalence. Circulation. 2006; 114:119-125
3. Haissaguerre M, Jais P, Shah D C, Takahashi A, Hocini M, Quiniou G, Garrigue S, Le Mouroux A, Le Metayer P, Clementy J. Spontaneous initiation of atrialfibrillation by ectopic beats originating in the pulmonary veins. N Engl J Med. 1998; 339:659-666
4. Haissaguerre M, Jais P, Shah D C, Garrigue S, Takahashi A, Lavergne T, Hocini M, Peng J T, Roudaut R, Clementy J. Electrophysiological end point for catheter ablation of atrial fibrillation initiated from multiple pulmonary venous foci. Circulation. 2000; 101.1409-1417
5. Cappato R, Calkins H, Chen S A, Davies W, Iesaka Y, Kalman J, Kim Y H, Klein G, Natale A, Packer D, Skanes A, Ambrogi F, Biganzoli E. Updated worldwide survey on the methods, efficacy, and safety of catheter ablation for human atrial fibrillation. Circ Arrhythm Electrophysiol.2010v332-38
6. Nademanee K, McKenzie J, Kosar E, Schwab M, Sunsaneewitayakul B, Vasavakul T, Khunnawat C, Ngarmukos T. A new approach for catheter ablation of atrial fibrillation: Mapping of the electrophysiologic substrate. J Am Coll Cardiol. 2004; 43:2044-2053
7. Atienza F, Almendral J, Jalife J, Zlochiver S, Ploutz-Snyder R, Torrecilla E G, Arenal A, Kalifa J, Fernandez-Aviles F, Berenfeld O. Real-time dominant frequency mapping and ablation of dominant frequency sites in atrial fibrillation with left-to-right frequency gradients predicts long-term maintenance of sinus rhythm. Heart Rhythm. 2009; 6:33-40
8. Narayan S M, Krummen D E, Shivkumar K, Clopton P, Rappel W J, Miller J M. Treatment of atrial fibrillation by the ablation of localized sources: Confirm (conventional ablation for atrial fibrillation with or without focal impulse and rotor modulation) trial. J Am Coll Cardiol. 2012; 60:628-636
9. Xu J, Cui G, Esmailian F, Plunkett M, Marelli D, Ardehali A, Odim J, Laks H, Sen L. Atrial extracellular matrix remodeling and the maintenance of atrial fibrillation. Circulation. 2004; 109:363-368
10. Mahnkopf C, Badger T J, Burgon N S, Daccarett M, Haslam T S, Badger C T, McGann C J, Akoum N, Kholmovski E, Macleod R S, Marrouche N F. Evaluation of the left atrial substrate inpatients with lone atrial fibrillation using delayed-enhanced MRI: Implications for disease progression and response to catheter ablation. Heart Rhythm. 2010; 7.1475-1481
11. Tanaka K, Zlochiver S, Vikstrom K L, Yamazaki M, Moreno J, Klos M, Zaitsev A V, Vaidyanathan R, Auerbach D S, Landas S, Guiraudon G, Jalife J, Berenfeld O, Kalifa J. Spatial distribution of fibrosis governs fibrillation wave dynamics in the posterior left atrium during heart failure. Circ Res. 2007; 101:839-847
12. McDowell K S, Vadakkumpadan F, Blake R, Blauer J, Plank G, MacLeod R, Trayanova N. Mechanistic inquiry into the role of tissue remodling in fibrotic lesions in human atrial fibrillation. Biophys J. 2013; 104:2764
13. Akoum N, Daccarett M, McGann C, Segerson N, Vergara G, Kuppahally S, Badger T, Burgon N, Haslam T, Kholmovski E, Macleod R, Marrouche N. Atrial fibrosis helps select the appropriate patient and strategy in catheter ablation of atrial fibrillation: A DE-MRI guided approach. J Cardiovasc Electrophysiol. 2011; 22; 16-22
14. McDowell K S, Vadakkumpadan F, Blake R, Blauer J, Plank G, Macleod R S, Trayanova N A. Methodology for patient-specific modeling of atrial fibrosis as a substrate for atrial fibrillation. J Electrocardiol. 2012; 45:640-645
15. Prassl A J, Kickinger F, Ahammer H, Grau V, Schneider J E, Hofer E, Vigmond E J, Trayanova N A, Plank G. Automatically generated, anatomically accurate meshes for cardiac electrophysiology problems. IEEE Trans Biomed Eng. 2 pp 9; 56:1318-1330
16. Vadakkumpadan F, Arevalo H, Ceritoglu C, Miller M, Trayanova N. Image based estimation of ventricular fiber orientations for personalized modeling of cardiac electrophysiology. IEEE Trans Med Imaging. 2012; 31:1051-1060
17. Courtemanche M, Ramirez R J, Nattel S. Ionic targets for drug therapy and atrial fibrillation-induced electrical remodeling: Insights from a mathematical model. Cardiovasc Res. 1999; 42:477-489
18. Krummen D E, Bayer J D, Ho J, Ho G, Smetak M R, Clopton P, Trayanova N A, Narayan S M. Mechanisms of human atrial fibrillation initiation: Clinical and computational studies of repolarization restitution and activation latency. Circ Arrhythm Electrophysiol. 2012; 5.1149-1159
19. Kneller J, Zou R Q, Vigmond E J, Wang Z G, Leon L J, Nattel S. Cholinergic atrial fibrillation in a computer model of a two-dimensional sheet of canine atrial cells with realistic ionic properties. Circulation Research. 2002; 90:E73-E87
20. Hanson A, Holm M, Blomstrom P, Johanson R, Luhrs C, Brandt J, Olsson S B. Right atrial free wall conduction velocity and degree of anisotropy in patients with stable sinus rhythm studied during open heart surgery. Eur Heart J. 1998; 19:293-300
21. Luo M H, Li Y S, Yang K P. Fibrosis of collagen i and. remodeling of connexin 43 in atrial myocardium of patients with atrial fibrillation. Cardiology. 2007; 107: 248-253
22. Kostin S, Klein G, Szalay Z, Hein S, Bauer E P, Schaper J. Structural correlate of atrial fibrillation in human patients. Cardiovasc Res. 2Q02; 54:361-379

23. Du J, Xie J, Zhang Z, Tsujikawa H, Fusco D, Silverman D, Liang B, Yue L. Trpm7-mediated cat+ signals confer fibrogenesis in human atrial fibrillation. Circ Res. 2010; 106:992-1Q03.
24. Camelliti P, Green C R, LeGrice I, Kohl P. Fibroblast network in rabbit sinoatrial node: Structural and functional identification of homogeneous and heterogeneous cell coupling. Circ Res. 2004; 94:828-835
25. McDowell K S, Arevalo H J, Maleckar M M, Trayanova N A. Susceptibility to arrhythmia in the infarcted heart depends on myofibroblast density. Biophys J. 2011; 101: 1307-1315
26. Vigmond E J, Hughes M, Plank G, Leon U. Computational tools for modeling electrical activity in cardiac tissue. J Electrocardiol. 2003; 36 Supp1:69-74
27. Byrd G D, Prasad S M, Ripplinger C M, Cassilly T R, Schuessler R B, Boineau J P, Damiano R J, Jr. Importance of geometry and refractory period in sustaining atrial fibrillation: Testing the critical mass hypothesis. Circulation. 2005; 112:I7-13
28. Miragoli M, Gaudesius G, Rohr S. Electrotonic modulation of cardiac impulse conduction by myofibroblasts. Circ Res. 2006; 98:801-810
29. Vasquez C, Mohandas P, Louie K L, Benamer N, Bapat A C, Morley G E. Enhanced fibroblast-myocyte interactions in response to cardiac injury. Circ Res. 2010; 107: 1011-1020
30. Kuo C S, Munakata K, Reddy C P, Surawicz B. Characteristics and possible mechanism of ventricular arrhythmia dependent on the dispersion of action potential durations. Circulation. 1983; 67:1356-1367
31. Sanchez J E, Kay G N, Benser M E, Hall J A, Walcott G P, Smith W M, Ideker R E. Identification of transmural necrosis along a linear catheter ablation lesion during atrial fibrillation and sinus rhythm. J Intery Card Electrophysiol. 2003; 8:9-17
32. Rook M B, Vanginneken A C G, Dejonge B, Elaoumari A, Gros D, Jongsma H J. Differences in gap junction channels between cardiac myocytes, fibroblasts, and heterologous pairs. American Journal of Physiology. 1992; 263:0959-0977
33. Pedrotty D M, Klinger R Y, Kirkton R D, Bursac N. Cardiac fibroblast paracrine factors alter impulse conduction and ion channel expression of neonatal rat cardiomyocytes. Cardiovasc Res. 2009; 83:688-697
34. Maleckar M M, Greenstein J L, Giles W R, Trayanova N A. Electrotonic coupling between human atrial myocytes and fibroblasts alters myocyte excitability and repolarization. BiophysJ. 2009; 97:2179-2190
35. Zlochiver S, Munoz V, Vikstrom K L, Taffet S M, Berenfeld O, Jalife J. Electrotonic myofibroblast-to-myocyte coupling increases propensity to reentrant arrhythmias in two-dimensional cardiac monolayers. Brophys J. 2008; 95:4469-4480
36. Morita N, Sovari A A, Xie Y, Fishbein M C, Mandel W J, Garfinkel A, Lin S F, Chen P S, Xie L H, Chen F, Qu Z, Weiss j N, Karagueuzian H S. Increased susceptibility of aged hearts to ventricular fibrillation during oxidative stress. Am J Physiol Heart Circ Physiol. 2009; 297: H1594-1605
37. Tanner H, Hindricks G, Kobza R, Dorszewski A, Schirdewahn P, Piorkowski C, Gerds-Li J H, Kottkamp H. Trigger activity more than three years after left atrial linear ablation without pulmonary vein isolation inpatients with atrial fibrillation. Journal of the American College of Cardiology. 2005; 46.338-343.
38. Daccarett M, McGann C J, Akoum N W, MacLeod R S, Marrouche N F. MRI of the left atrium: Predicting clinical outcomes inpatients with atrial fibrillation. Expert review of cardiovascular therapy. 2011; 9:105-111.
39. Khurram I M, Beinart R, Zipunnikov V, Dewire J, Yarmohammadi H, Sasaki T, et al. Magnetic resonance image intensity ratio, a normalized measure to enable interpatient comparability of left atrial fibrosis. Heart Rhythm. 2014; 11(1):85-92.
40. Oakes R S, Badger T J, Kholmovski E G, Akoum N, Burgon N S, Fish E N, et al. Detection and quantification of left atrial structural remodeling with delayed-enhancement magnetic resonance imaging in patients with atrial fibrillation. Circulation. 2009; 119(13):1758-67.
41. Seg3D C. Volumetric Image Segmentation and Visualization. Scientific Computing and Imaging Institute (SCI). 2013.
42. Verma A, Wazni O M, Marrouche N F, Martin D O, Kilicaslan F, Minor S, et al. Pre-existent left atrial scarring in patients undergoing pulmonary vein antrum isolation: an independent predictor of procedural failure. J Am Coll Cardiol. 2005; 45(2):285-92.
43. Raya S P, Udupa J K. Shape-based interpolation of multidimensional objects. IEEE Trans Med Imaging. 1990; 9(1):32-42.
44. Prassl A J, Kickinger F, Ahammer H, Grau V, Schneider J E, Hofer E, et al. Automatically generated, anatomically accurate meshes for cardiac electrophysiology problems. IEEE Trans Biomed Eng. 2009; 56(5):1318-30.
45. Krueger M, Schmidt V, Tobon C, Weber F, Lorenz C, Keller D J, et al. Modeling Atrial Fiber Orientation in Patient-Specific Geometries: A Semi-automatic Rule-Based Approach. In: Metaxas D, Axel L, editors. Functional Imaging and Modeling of the Heart: Springer Berlin Heidelberg; 2011. p. 223-32.
46. McDowell K S, Vadakkumpadan F, Blake R, Blauer J, Plank G, MacLeod R S, et al. Methodology for patient-specific modeling of atrial fibrosis as a substrate for atrial fibrillation. J Electrocardiol. 2012; 45(6):640-5.
47. McDowell K S, Zahid S, Vadakkumpadan F, Blauer J, MacLeod R S, Trayanova N A. Virtual electrophysiological study of atrial fibrillation in fibrotic remodeling. PLoS One. 2015; 10(2):e0117110
48. McDowell K S, Zahid S, Vadakkumpadan F, Blauer J, MacLeod R S, Trayanova N A. Virtual electrophysiological study of atrial fibrillation in fibrotic remodeling. PLoS One. 2015; 10(2):e0117110.
49. Courtemanche M, Ramirez R J, Nattel S. Ionic mechanisms underlying human atrial action potential properties: insights from a mathematical model. Am J Physiol. 1998; 275(1 Pt 2):H301-21
50. Courtemanche M, Ramirez R J, Nattel S. Ionic targets for drug therapy and atrial fibrillation-induced electrical remodeling: insights from a mathematical model. Cardiovasc Res. 1999; 42(2):477-89.
51. Krummen D E, Bayer J D, Ho J, Ho G, Smetak M R, Clopton P, et al. Mechanisms of human atrial fibrillation initiation: clinical and computational studies of repolarization restitution and activation latency. Circ Arrhythm Electrophysiol. 2012; 5(6) 1149-59
52. Itoh T, Kimura M, Sasaki S, Owada S, Horiuchi D, Sasaki K, et al. High correlation of estimated local conduction velocity with natural logarithm of bipolar electrogram amplitude in the reentry circuit of atrial flutter. J Cardiovasc Electrophysiol. 2014; 25(4):387-94

53. Nattel S, Burstein B, Dobrev D. Atrial remodeling and atrial fibrillation: mechanisms and implications. Circ Arrhythm Electrophysiol. 2008; 1(1):62-73.
54. Corradi D, Callegari S, Maestri R, Benussi S, Alfieri O. Structural remodeling in atrial fibrillation. Nat Clin Pract Cardiovasc Med. 2008; 5(12):782-96.
55. Kakkar R, Lee R T. Intramyocardial fibroblast myocyte communication. Circ Res. 2010; 106(1):47-57.
56. He X, Gao X, Peng L, Wang S, Zhu Y, Ma H, et al. Atrial fibrillation induces myocardial fibrosis through angiotensin II type 1 receptor-specific Arkadia-mediated downregulation of Smad7. Circ Res. 2011; 108(2):164-75.
57. Heijman J, Voigt N, Nattel S, Dobrev D. Cellular and molecular electrophysiology of atrial fibrillation initiation, maintenance, and progression. Circ Res. 2014; 114 (9): 1483-99.
58. Avila G, Medina I M, Jimenez E, Elizondo G, Aguilar C I. Transforming growth factor-beta1 decreases cardiac muscle L-type Ca2+ current and charge movement by acting on the Cav1.2 mRNA. Am J Physiol Heart Circ Physiol. 2007; 292(1):H622-31
59. Ramos-Mondragon R, Galindo C A, Avila G. Role of TGF-beta on cardiac structural and electrical remodeling. Vasc Health Risk Manag. 2008; 4(6):1289-300.
60. Ramos-Mondragon R, Vega A V, Avila G. Long-term modulation of Na+ and K+ channels by TGF-beta1 in neonatal rat cardiac myocytes. Pflugers Arch. 2011; 461 (2):235-47.
61. Pedrotty D M, Klinger R Y, Kirkton R D, Bursae N. Cardiac fibroblast paracrine factors alter impulse conduction and ion channel expression of neonatal rat cardiomyocytes. Cardiovasc Res. 2009; 83(4):688-97.
62. Li D, Fareh S, Leung T K, Nattel S. Promotion of atrial fibrillation by heart failure in dogs: atrial remodeling of a different sort. Circulation. 1999; 100(1):87-95.
63. Luo M H, Li Y S, Yang K P. Fibrosis of collagen I and remodeling of connexin 43 in atrial myocardium of patients with atrial fibrillation. Cardiology. 2007; 107(4): 248-53.
64. Kostin S, Klein G, Szalay Z, Hein S, Bauer E P, Schaper J. Structural correlate of atrial fibrillation in human patients. Cardiovasc Res. 2002; 54(2):361-79.
65. Burstein B, Comtois P, Michael G, Nishida K, Villeneuve L, Yeh Y H, et al. Changes in connexin expression and the atrial fibrillation substrate in congestive heart failure. Circ Res. 2009; 105(12):1213-22.
66. Vigmond E J, Aguel F, Trayanova N A. Computational techniques for solving the bidomain equations in three dimensions. IEEE Trans Biomed Eng. 2002; 49(11):1260-9.
67. Boykov Y, Kolmogorov V. An experimental comparison of min-cut/max-flow algorithms for energy minimization in vision. IEEE Trans Pattern Anal Mach Intel. 2004; 26(9):1124-37.
68. Cummings J E, Schweikert R, Saliba W, Hao S, Martin D O, Marrouche N F, Burkhardt J D, Kilicaslan F, Verma A, Beheiry S, Belden W and Natale A. Left atrial flutter following pulmonary vein antrum isolation with radiofrequency energy: linear lesions or repeat isolation. Journal of cardiovascular electrophysiology. 2005; 16:293-7.
69. Duru F, Hindricks G and Kottkamp H. Atypical left atrial flutter after intraoperative radiofrequency ablation of chronic atrial fibrillation: successful ablation using three-dimensional electroanatomic mapping. Journal of cardiovascular electrophysiology. 2001; 12:602-5.
70. Mama G, Pedrinazzi C, Durin O, Agricola P, Romagnoli G and Gazzaniga P. Usefulness and limitations of the surface electrocardiogram in the classification of right and left atrial flutter. Journal of cardiovascular medicine. 2006; 7:381-7.
71. Usui A, Inden Y, Mizutani S, Takagi Y, Akita T and Ueda Y. Repetitive atrial flutter as a complication of the left-sided simple maze procedure. The Annals of thoracic surgery. 2002; 73:1457-9.
72. Villacastin J, Perez-Castellano N, Moreno J and Gonzalez R. Left atrial flutter after radiofrequency catheter ablation of focal atrial fibrillation. Journal of cardiovascular electrophysiology. 2003; 14:417-21.
73. Sawhney N, Anousheh R, Chen W and Feld G K. Circumferential pulmonary vein ablation with additional linear ablation results in an increased incidence of left atrial flutter compared with segmental pulmonary vein isolation as an initial approach to ablation of paroxysmal atrial fibrillation. Circulation Arrhythmia and electrophysiology. 2010; 3:243-8.
74. Oral H, Knight B P and Morady F. Left atrial flutter after segmental ostial radiofrequency catheter ablation for pulmonary vein isolation. Pacing and clinical electrophysiology: PACE. 2003; 26:1417-9.
75. Gerstenfeld E P, Callans D J, Dixit S, Russo A M, Nayak H, Lin D, Pulliam W, Siddique S, Marchlinski F E. Mechanisms of organized left atrial tachycardias occurring after pulmonary vein isolation. Circulation Sep. 14, 2004; 110:1351-1357.
76. Daoud E G, Weiss R, Augostini R, Hummel J D, Kalbfleisch S J, Van Deren J M, Dawson G, Bowman K. Proarrhythmia of circumferential left atrial lesions for management of atrial fibrillation. Journal of cardiovascular electrophysiology February 2006; 17:157-165.
77. Weerasooriya R, Jais P, Wright M, Matsuo S, Knecht S, Nault I, Sacher F, Deplagne A, Bordachar P, Hocini M, Haissaguerre M. Catheter ablation of atrial tachycardia following atrial fibrillation ablation. Journal of cardiovascular electrophysiology July 2009; 20:833-838.
78. Miyazaki S, Shah A J, Kobori A, Kuwahara T, Takahashi A. How to approach reentrant atrial tachycardia after atrial fibrillation ablation. Circulation Arrhythmia and electrophysiology February 2012; 5:e1-7.
79. Stevenson W G, Sager P T, Friedman P L. Entrainment techniques for mapping atrial and ventricular tachycardias. Journal of cardiovascular electrophysiology March 1995; 6:201-216.
80. Patel A M, d'Avila A, Neuzil P, Kim S J, Mela T, Singh J P, Ruskin J N, Reddy V Y. Atrial tachycardia after ablation of persistent atrial fibrillation: identification of the critical isthmus with a combination of multielectrode activation mapping and targeted entrainment mapping. Circulation Arrhythmia and electrophysiology April 2008; 1:14-22.
81. Jais P, Shah D C, Haissaguerre M, Hocini M, Peng J T, Takahashi A, Garrigue S, Le Metayer P, Clementy J. Mapping and ablation of left atrial flutters. Circulation Jun. 27, 2000; 101:2928-2934.
82. Khurram I M, Beinart R, Zipunnikov V, et al. Magnetic resonance image intensity ratio, a normalized measure to enable interpatient comparability of left atrial fibrosis. Heart rhythm: the official journal of the Heart Rhythm Society January 2014; 11:85-92.
83. McDowell K S, Vadakkumpadan F, Blake R, Blauer J, Plank G, MacLeod R S, Trayanova N A. Methodology for patient-specific modeling of atrial fibrosis as a substrate for atrial fibrillation. Journal of electrocardiology November-December 2012; 45:640-645.

84. Vadakkumpadan F, Arevalo H, Ceritoglu C, Miller M, Trayanova N. Image-based estimation of ventricular fiber orientations for personalized modeling of cardiac electrophysiology. IEEE transactions on medical imaging May 2012; 31:1051-1060.
85. Courtemanche M, Ramirez R J, Nattel S. Ionic mechanisms underlying human atrial action potential properties: insights from a mathematical model. The American journal of physiology July 1998; 275:H301-321.
86. Krummen D E, Bayer J D, Ho J, Ho G, Smetak M R, Clopton P, Trayanova N A, Narayan M. Mechanisms of human atrial fibrillation initiation: clinical and computational studies of repolarization restitution and activation latency. Circulation Arrhythmia and electrophysiology December 2012; 5:1149-1159.
87. Ramos-Mondragon R, Galindo C A, Avila G. Role of TGF-beta on cardiac structural and electrical remodeling. Vascular health and risk management 2008; 4:1289-1300.
88. Itoh T, Kimura M, Sasaki S, Owada S, Horiuchi D, Sasaki K, Ishida Y, Takahiko K, Okumura K. High correlation of estimated local conduction velocity with natural logarithm of bipolar electrogram amplitude in the reentry circuit of atrial flutter. Journal of cardiovascular electrophysiology April 2014; 25:387-394.
89. Vigmond E J, Aguel F, Trayanova N A. Computational techniques for solving the bidomain equations in three dimensions. IEEE transactions on bio-medical engineering November 2002; 49:1260-1269.
90. Boykov Y, Kolmogorov V. An experimental comparison of min-cut/max-flow algorithms for energy minimization in vision. IEEE transactions on pattern analysis and machine intelligence September 2004; 26:1124-1137.
91. Ouyang F, Ernst S, Vogtmann T, Goya M, Volkmer M, Schaumann A, Bansch D, Antz M, Kuck K H. Characterization of reentrant circuits in left atrial macroreentrant tachycardia: critical isthmus block can prevent atrial tachycardia recurrence. Circulation Apr. 23, 2002; 105: 1934-1942.
92. Boyden P A, Tilley L P, Albala A, Liu S K, Fenoglio J J, Jr., Wit A L. Mechanisms for atrial arrhythmias associated with cardiomyopathy: a study of feline hearts with primary myocardial disease. Circulation May 1984; 69:1036-1047.
93. Boykov Y, Funka-Lea G. Graph cuts and efficient ND image segmentation. Int J Comput Vision 2006; 70:109-131.
94. Baker B M, Lindsay B D, Bromberg B I, Frazier D W, Cain M E, Smith J M. Catheter ablation of clinical intraatrial reentrant tachycardias resulting from previous atrial surgery: localizing and transecting the critical isthmus. Journal of the American College of Cardiology 1996; 28:411-417.
96. Rostock T, Drewitz I, Steven D, Hoffmann B A, Salukhe T V, Bock K, Servatius H, Aydin M A, Meinertz T, Willems S. Characterization, mapping, and catheter ablation of recurrent atrial tachycardias after stepwise ablation of long-lasting persistent atrial fibrillation. Circulation Arrhythmia and electrophysiology April 2010; 3:160-169.
97. Ashikaga H, Arevalo H, Vadakkumpadan F, et al. Feasibility of image-based simulation to estimate ablation target in human ventricular arrhythmia. Heart rhythm: the official journal of the Heart Rhythm Society August 2013; 10:1109-1116.
98. Knowles B R, Batchelor P G, Parish V, Ginks M, Plein S, Razavi R, Schaeffter T. Pharmacokinetic modeling of delayed gadolinium enhancement in the myocardium. Magnetic resonance in medicine December 2008; 60:1524-1530.

The above provides some examples according to particular embodiments of the current invention. The broad concepts of the current invention are not limited to only these particular examples.

The three-dimensional imaging data can be MRI data as described in the examples above. However, the broad concepts of the current invention are not limited to that particular example. The three-dimensional imaging data can be can be at least one of magnetic resonance imaging (MRI), computed tomography (CT), positron emission tomography (PET), ultrasound, or nuclear tracer three-dimensional imaging data, for example. The method for identifying one or more ablation locations in an atrial tissue region can further include receiving additional patient-specific data in addition to the three-dimensional imaging data. For example, some embodiments can include receiving at least one of biopsy data, electrocardiogram data, recorded data from an implantable device (pace maker, defibrillator, etc.), or invasive electrical mapping data (e.g., endoscopic). The simulating can then use the additional patient-specific data for the simulation.

The simulating may include simulating at least one or both of electrophysiological or electromechanical activity of the atria or a portion of them. Simulating at least one of electrophysiological or electromechanical activity of the atria or a portion of them can include constructing a geometric model of the atria or a portion of them. The geometric model can include normal tissue regions and remodeled atrial tissue regions that are determined for the patient using the three-dimensional imaging data. The term "remodeled tissue" can include fibrosis, infarct scar, infarct border (gray) zone, or other disease-related structural, electrophysiological or contractile changes in the tissue. The simulating can further include estimating tissue fiber orientations in the geometric model of the atria. The estimation of fiber orientations can be done in a variety of ways. For example, the fiber orientations can be calculated using a Laplace-Dirichlet method to define the local axes at each spatial location in the atria (J. D. Bayer, R. Blake, G. Plank, Trayanova N, Novel rule based algorithm for assigning myocardial fiber orientation to computation heart models. *Ann Biomed Eng* (2012), the entire contents of which are incorporated herein by reference). Another approach could utilize pre-compiled data (i.e., atlas data), which can be mapped into the specific size and shape of the patient's heart (Image-Based Estimation of Ventricular Fiber Orientations for Personalized Modeling of Cardiac Electrophysiology, Vadakkumpadan F, Arevalo H, Ceritoglu C, Miller M, Trayanova N., IEEE Trans Med Imaging. Jan. 18, 2012 (the entire contents of which are incorporated herein by reference).

The geometric model of the tissue region may include at least a geometric model of right and left atria of the patient's heart. The remodeled tissue regions in this case can be segmented into a plurality of different regions based on the three-dimensional imaging data. The plurality of different regions can include fibrotic regions, scar tissue regions, normal tissues regions, and transition zones, for example, between normal and fibrotic tissue regions. The simulating in this case can be simulating electrophysiological activity of at least the right and left atria of the patient's heart.

The geometric model of the tissue region may include a geometric model of at least right and left atria of the patient's heart. In this embodiment, the remodeled tissue regions are fibrotic tissue regions. The simulating at least one of electrophysiological or electromechanical activity is simulating electrophysiological activity of at least the right and left atria of the patient's heart. The remodeled tissue regions can include changes in property that are more or less pronounced, or represent different degrees of fibrosis.

Numerous specific details have been set forth to provide a thorough understanding of the embodiments. It will be understood, however, that the embodiments may be practiced without these specific details. In other instances, well-known operations, components, and circuits have not been described in detail so as not to obscure the embodiments. It can be appreciated that the specific structural and functional details are representative and do not necessarily limit the scope of the embodiments.

Although some embodiments may be illustrated and described as comprising examples of functional components or modules performing various operations, it can be appreciated that such components or modules may be implemented by one or more hardware components, software components, and/or combination thereof. The functional components and/or modules may be implemented, for example, by logic (e.g., instructions, data, and/or code) to be executed by a logic device (e.g., processor). Such logic may be stored internally or externally to a logic device on one or more types of computer-readable storage media.

Some embodiments may comprise an article of manufacture. An article of manufacture may comprise a storage medium to store logic. Examples of a storage medium may include one or more types of computer-readable storage media capable of storing electronic data, including volatile memory or non-volatile memory, removable or non-removable memory, erasable or non-erasable memory, writeable or re-writeable memory, and so forth. Examples of storage media include hard drives, disk drives, solid state drives, and any other tangible or non-transitory storage media.

It also is to be appreciated that the described embodiments illustrate example implementations, and that the functional components and/or modules may be implemented in various other ways, which are consistent with the described embodiments. Furthermore, the operations performed by such components or modules may be combined and/or separated for a given implementation and may be performed by a greater number or fewer number of components or modules.

Some of the figures may include a flow diagram. Although such figures may include a particular logic flow, it can be appreciated that the logic flow merely provides an example implementation of the general functionality. Further, the logic flow does not necessarily have to be executed in the order presented unless otherwise indicated. In addition, the logic flow may be implemented by a hardware element, a software element executed by a processor, or any combination thereof.

The embodiments discussed in this specification are intended to explain concepts of the invention. However, the invention is not intended to be limited to the specific terminology selected and the particular examples described. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A computer-implemented method for non-invasively identifying ablation locations in atrial tissue, comprising:

receiving three-dimensional imaging data representing atrial tissue of a left atrial flutter (LAFL) subject, wherein said atrial tissue includes at least one of a left atrium and a right atrium;

generating a subject-specific model of said at least one of said atrial tissue from said three-dimensional imaging data;

estimating tissue fiber orientations in said atrial tissue;

assigning said estimated tissue fiber orientations to said subject-specific model of said atrial tissue;

conducting simulations of LAFL using the subject-specific model to identify 1) regions of slow conduction of a propagating wave within an atrial tissue region of said atrial tissue; 2) a critical isthmus of a rotational wavefront within said atrial tissue region; or 3) a region based on a minimum cut in a flow network;

identifying at least one ablation location in the atrial tissue region based on at least one of said identified regions of slow conduction, said critical isthmus, or said minimum cut;

wherein identifying the at least one ablation location includes identifying one or more ablation lesion locations and at least one line connecting said one or more lesion locations with a nearest non-conductive anatomical barrier;

wherein the non-conductive anatomical barrier is a pulmonary vein or an ablation lesion from a pulmonary vein isolation procedure that encircled the pulmonary vein;

identifying connecting targets where transection lesion endpoints must extend so that a wave cannot propagate around the lesion; and wherein said pulmonary vein isolation ablation is executed prior to extending said ablation lesion to said connecting targets.

2. The method of claim 1, wherein said at least said atrial tissue includes both said left atrium and said right atrium.

3. The method of claim 1, wherein said generating said subject-specific model further comprises identifying normal tissue regions and remodeled tissue regions of said three-dimensional imaging data and assigning tissue properties to said normal tissue regions and said remodeled tissue regions.

4. The method of claim 3, wherein the remodeled tissue regions includes a plurality of degrees of fibrosis.

5. The method of claim 1, wherein said identifying at least one ablation location in the atrial tissue region identifies at least one ablation location to render the subject non-inducible for LAFL.

6. The method of claim 1, wherein said generating said subject-specific model of said atrial tissue region includes a representation of an ablation lesion in said subject from a previous procedure.

7. The method of claim 1, wherein the non-conductive anatomical barrier is a mitral valve.

8. A non-transient computer-readable medium comprising computer-executable code that, when executed by a computer, causes the computer to perform:

receiving three-dimensional imaging data representing atrial tissue of a left atrial flutter (LAFL) subject, wherein said atrial tissue includes at least one of a left atrium and a right atrium;

generating a subject-specific model of said at least one of said atrial tissue from said three-dimensional imaging data;

estimating tissue fiber orientations in said atrial tissue;

assigning said estimated tissue fiber orientations to said subject-specific model of said atrial tissue;

conducting simulations of LAFL using the subject-specific model to identify 1) regions of slow conduction of a propagating wave within an atrial tissue region of said atrial tissue; 2) a critical isthmus of a rotational wavefront within said atrial tissue region; or 3) a region based on a minimum cut in a flow network;

identifying at least one ablation location in the atrial tissue region based on at least one of said identified regions of slow conduction, said critical isthmus, or said minimum cut;

wherein said generating said subject-specific model of said atrial tissue region includes a representation of an ablation lesion in said subject from a previous procedure;

wherein said identifying the at least one ablation location includes identifying one or more ablation lesion locations and at least one line connecting said one or more lesion locations with a nearest non-conductive anatomical barrier;

wherein the non-conductive anatomical barrier is a pulmonary vein or an ablation lesion from a pulmonary vein isolation procedure that encircled the pulmonary vein;

identifying connecting targets where transection lesion endpoints must extend so that a wave cannot propagate around the lesion; and wherein said pulmonary vein isolation ablation is executed prior to extending said ablation lesion to said connecting targets.

9. The non-transient computer-readable medium of claim 8, wherein said at least said atrial tissue includes both said left atrium and said right atrium.

10. The non-transient computer-readable medium of claim 8, wherein said generating said subject-specific model further comprises identifying normal tissue regions and remodeled tissue regions of said three-dimensional imaging data and assigning tissue properties to said normal tissue regions and said remodeled tissue regions.

11. The non-transient computer-readable medium of claim 10, wherein the remodeled tissue regions includes a plurality of degrees of fibrosis.

12. The non-transient computer-readable medium of claim 8, wherein said identifying at least one ablation location in the atrial tissue region identifies at least one ablation location to render the subject non-inducible for LAFL.

13. The non-transient computer-readable medium of claim 8, wherein the non-conductive anatomical barrier is a mitral valve.

14. A computer-implemented method for non-invasively identifying ablation locations in atrial tissue, comprising:
    receiving three-dimensional imaging data representing atrial tissue of a left atrial flutter (LAFL) subject, wherein said atrial tissue includes at least one of a left atrium and a right atrium;
    generating a subject-specific model of said at least one of said atrial tissue from said three-dimensional imaging data;
    estimating tissue fiber orientations in said atrial tissue;
    assigning said estimated tissue fiber orientations to said subject-specific model of said atrial tissue;
    conducting simulations of LAFL using the subject-specific model to identify 1) regions of slow conduction of a propagating wave within an atrial tissue region of said atrial tissue; 2) a critical isthmus of a rotational wavefront within said atrial tissue region; or 3) a region based on a minimum cut in a flow network; and
    identifying at least one ablation location in the atrial tissue region based on at least one of said identified regions of slow conduction, said critical isthmus, or said minimum cut;
    wherein identifying the at least one ablation location includes identifying one or more ablation lesion locations and at least one line connecting said one or more lesion locations with a nearest non-conductive anatomical barrier; and
    identifying connecting targets where transection lesion endpoints must extend so that a wave cannot propagate around the lesion.

* * * * *